(12) United States Patent
Martin, Jr. et al.

(10) Patent No.: US 8,603,799 B2
(45) Date of Patent: Dec. 10, 2013

(54) **GROWTH ENHANCEMENT AND CONTROL OF BACTERIAL AND FUNGAL PLANT DISEASES WITH *STREPTOMYCES SCOPULIRIDIS***

(75) Inventors: William R. Martin, Jr., Canandaigua, NY (US); Nicole J. Scott, Clifton Springs, NY (US)

(73) Assignee: Bioworks, Inc., Victor, NY (US)

( * ) Notice: Subject to any disclaimer, the term of this patent is extended or adjusted under 35 U.S.C. 154(b) by 0 days.

(21) Appl. No.: 13/194,000

(22) Filed: Jul. 29, 2011

(65) Prior Publication Data

US 2012/0028799 A1 Feb. 2, 2012

Related U.S. Application Data

(60) Provisional application No. 61/369,315, filed on Jul. 30, 2010.

(51) Int. Cl.
*A01N 63/00* (2006.01)

(52) U.S. Cl.
USPC ........................................ 435/253.5; 504/101

(58) Field of Classification Search
USPC ........................................ 435/253.5; 504/101
See application file for complete search history.

(56) References Cited

U.S. PATENT DOCUMENTS

| 6,274,157 | B1 | 8/2001 | Lai et al. | |
|---|---|---|---|---|
| 6,524,577 | B1* | 2/2003 | Lehman et al. | 424/93.43 |
| 6,991,820 | B2 | 1/2006 | Ming et al. | |
| 7,226,590 | B2 | 6/2007 | Chilcott et al. | |
| 7,247,306 | B2 | 7/2007 | Fliss et al. | |
| 2008/0248953 | A1* | 10/2008 | Smith et al. | 504/100 |
| 2010/0286030 | A1 | 11/2010 | Farris | |

FOREIGN PATENT DOCUMENTS

| CN | 1 566 109 A | 1/2005 |
|---|---|---|
| WO | 2009/045234 A1 | 4/2009 |

OTHER PUBLICATIONS

Smith et al., How to make hydroponic solutions, <http://www.ehow.com/how_5600928_make-hydroponic-solution.html>, downloaded Sep. 24, 2013.*
Schrey et al., "Friends and Foes: Streptomycetes as Modulators of Plant Disease and Symbiosis," Antonie van Leeuwenhoek 94:11-19 (2008).
International Search Report and Written Opinion for corresponding PCT/US2011/045886 (Mar. 26, 2012).
Farris et al., "*Streptomyces scopuliridis* sp. nov., A Bacteriocin-Producing Soil Streptomycete," with Supplementary Materials, Int. J. Syst. Evol. Microbiol. 61(Pt 9):2112-2116 (published online Sep. 24, 2010).
Farris et al., "Purification and Characterization of a Bacteriolytic Enzyme Produced by a Soil Streptomyces Isolate," Abstracts of the General Meeting of the American Society for Microbiology, 107:427, N-036 (2007) (Abstract).
Poster Presentation, Farris et al., "Purification and Characterization of a Bacteriolytic Enzyme Produced by a Soil Streptomyces Isolate," N-036, 107th General Meeting of the American Society for Microbiology, Toronto, Canada (May 2007).
Tagg et al., "Bacteriocins of Gram Positive Bacteria," Bacteriol. Rev. 40(3):722-756 (1976).
EMBL Database Accession No. EF063457 (Nov. 26, 2006).
NCBI Database Accession No. ZP_01189115 (Mar. 6, 2006).
GenBank Database Accession No. EF657884 (Jul. 8, 2007).
International Search Report and Written Opinion for PCT/US2008/006279 (Sep. 15, 2008).
Official Action for Application No. MX/a/2010/003672 dated Jun. 7, 2012.
Office Action for Application No. EP 08 754 501.8 dated Oct. 30, 2012.
Abrahmsen et al., "Engineering subtilisin and its substrates for efficient ligation of peptide bonds in aqueous solution," Biochemistry, 30(17):4151-4159 (1991).
Abrioue et al., "Influence of physico-chemical factors on the oligomerization and biological activity of bacteriocin AS-48," Curr. Microbiol., 42:89-95 (2001).
Ainsa et al., "WhiA, a protein of unknown function conserved among gram-positive bacteria, is essential for sporulation in *Streptomyces coelicolor* A3(2)," J. of Bacteriology, 182:5470-5478 (2000).
Akesson et al., "Targeting of streptococci by zoocin A," FEMS Microbiology Letters, 270:155-161 (2007).
Baggiolini et al., "Interleukin-8, a chemotactic and inflammatory cytokine," FEBS Lett., 307(1):97-101 (1992).
Beukes, et al. "Purification and partial characterization of a murein hydrolase, millericin B, produced by *Streptococcus milleri* NMSCC 061," Appl. Environmental Microbiol., 66:23-28 (2000).
Branen et al., "Enhancement of nisin, lysozyme, and monolaurin antimicrobial activities by ethylenediaminetetraacetic acid and lactoferrin," Int'l. J. Food Microbiol., 90:63-74 (2004).
Caridi, "Selection of *Escherichia coli*-inhibiting strains of *Lactobacillus paracasei* subsp. Paracasei," J. Industrial Microbiol. Biotechnol., 29:303-308 (2002).

(Continued)

*Primary Examiner* — Susan Hanley
*Assistant Examiner* — Damon B Bowe
(74) *Attorney, Agent, or Firm* — LeClairRyan, A Professional Corporation

(57) ABSTRACT

Methods of controlling plant diseases mediated by bacterial or fungal plant pathogens. The method comprises providing *Streptomyces scopuliridis* strain RB72 or an isolated protein or polypeptide comprising the amino acid of SEQ ID NO:1 and applying the *Streptomyces scopuliridis* strain RB72 or the isolated protein or polypeptide comprising the amino acid of SEQ ID NO:1 to plants or plant seeds under conditions effective to treat plant diseases mediated by bacterial or fungal plant pathogens. Also disclosed is a plant or plant seed treated by this method, a planting composition, and a method of enhancing growth.

6 Claims, 5 Drawing Sheets

(56) References Cited

OTHER PUBLICATIONS

Castellano et al., "Inhibition of Listeria innocua and Brochothrix thermosphacta in vacuum-packaged meat by addition of bacteriocinogenic *Lactobacillus curvatus* CRL705 and its bacteriocins," Letters in Applied Microbiology, 43:194-199 (2006).
Chater, "Genetics of differentiation in Streptomyces," Annual Review of Microbiology, 47:685-713 (1993).
Chater, "A morphological and genetic mapping study of white colony mutants of *Streptomyces coelicolor*," J. of General Microbiology, 72:9-28 (1972).
Chater, "Regulation of sporulation in *Streptomyces coelicolor* A3(2): a checkpoint multiplex?" Curr. Opin. Microbiol., 4:667-673 (2001).
Chen et al., "Albusin B, a bacteriocin from the ruminal bacterium Ruminococcus albus 7 that inhibits growth of *Ruminococcus flavefticiens*," Appl. Environmental Microbiol., 70:3167-3170 (2004).
Claessen et al., "Regulation of Streptomyces development: reach for the sky!" Trends in Microbiol., 14:313-319 (2006).
Clark-Lewis et al., "Structural requirements for interleukin-8 function identified by design of analogs and CXC chemokine hybrids," J. Biol.Chem., 269(23):16075-16081 (1994).
Clark-Lewis et al., Chemical Synthesis, Purification, and Characterization of Two Inflammatory Proteins, Neutrophil Activating Peptide 1 (interleukin-8) and Neutrophil Activating Peptide 2, Biochemistry, 30:3128-3135 (1991).
Dawson et al., "Synthesis of Proteins by Native Chemical Ligation," Science, 266:776-779 (1994).
DeKwaadsteniet et al., "Characterization of a 3944 Da bacteriocin, produced by *Enterococcus mundtii* STI5, with activity against gram-positive and gram-negative bacteria," Int'l J. of Food Microbiol., 105:433-444 (2005).
Delves-Broughton et al., "Applications of the bacteriocin, nisin," Antonie Van Leeuwenhoek, 69:193-202 (1996).
Diep, et al., "Ribosomally synthesized antibacterial peptides in Gram-positive bacteria," Curr. Drug Targets, 3:107-122 (2002).
Dongre et al., "Emerging tandem-mass-spectrometry techniques for the rapid identification of proteins," Trends in Biotechnol., 15:418-425 (1997).
Embly et al., "The molecular phylogeny and systematic of the actinomycetes," Ann. Rev. Microbiol. 48:257-289 (1994).
Farris et al., "Detection of Actinobacteri a cultivated from environmental samples reveals bias in universal primers," Letters in Applied Microbiology, 45:376-81 (2007).
Felsenstein, "Evolutionary trees from DNA sequences: a maximum likelihood approach," J. of Mol. Evol., 17:368-376 (1981).
Gehring et al., "Genomewide insertional mutagenesis in *Streptomyces coelicolor* reveals additional genes involved in morphological differentiation," Proceedings of the National Academy of Sciences USA, 97:9642-9647 (2000).
Gillor et al., "Genetically engineered bacteriocins and their potential as the next generation of antimicrobials," Curr. Pharma. Design, 11:1067-1075 (2005).
Grant R15GM069402-01 awarded by the National Institutes of Health (2003).
Green et al., "Pediocin PD-1, a bactericidal antimicrobial peptide from Pediococcus damnosus NCFB 1832," J. Appl. Microbiol., 83:127-132 (1997).
Guinane et al., "Microbial solutions to microbial problems; lactococcal bacteriocins for the control of undesirable biota in food," J. Appl. Microbiol., 98:1316-1325 (2005).
Hain et al., "Discrimination of *Streptomyces albidoflavus* strains based on the size and number of 16S-2S ribosomal DNA intergenic spacers," Int'l. J. Systematic Bacteriol., 47:202-206 (1997).
Hall, "BioEdit: a user-friendly biological sequence alignment editor and analysis program for Windows 95/98/NT," Nucleic Acids Symposium Series, 41:95-98 (1999).
Hatano et al., "Taxonomic re-evaluation of whorl-forming Streptomyces (formerly Streptoverticillium) species by using phenotypes, DNA-DNA hybridization and sequence of gyrB, and proposal of *Streptomyces luteireticuli* (ex Katoh and Arai 1957) corrig., sp. nov., nom. rev.," Int'l J. of Systematic and Evolutionary Microbiology,53:1519-1529 (2003).
Heng et al., "The diversity of bacteriocins in gram-positive bacteria," In M. A. Riley and M. A. Chavan (cd.), Bacteriocins: ecology and evolution, SpringerVerlag, Heidelberg, Germany, pp. 45-92 (2007).
Heng et al., "Dysgalacticin: a novel, plasmid-encoded antimicrobial protein (bacteriocin) produced by *Streptococcus dysgalactiae* subsp. Equisimilis," Microbiology, 152:1991-2001 (2006).
Hert et al., "Relative importance of bacteriocin-like genes in antagonism of *Xanthomonas perforans* tomato race 3 to *Xanthomonas euvesicatoria* tomato race 1 strains," Appl. and Environ. Microbiology, 71:3581-3588 (2005).
Hickey et al., "Production of enterolysin A by a raw milk enterococcal isolate exhibiting multiple virulence factors," Microbiology, 149:655-664 (2003).
Hobbs et al., "Dispersed growth of Streptomyces in liquid culture," Appl. Microbiol. Biotechnol., 31:272-277 (1989).
Hopwood et al., "Mutants of *Streptomyces coelicolor* defective in sporulation," J. of General Microbiology, 61:397-408 (1970).
Hopwood, "Phase-contrast observations on *Streptomyces coelicolor*," J. of General Microbiology, 22:295-302 (1960).
Ivanova et al., "Characterization of a bacteriocin produced by *Streptococcus thermophilus* 81," Int'l. J. Food Microbiol., 42: 147-158 (1998).
Jack et al., "Bacteriocins of gram-positive bacteria," Microbiol. Rev., 59:171-200 (1995).
Joerger et al., "Characterization and purification of helveticin J and evidence for a chromosomally determined bacteriocin produced by *Lactobacillus helveticus* 481," J. of Bacteriology, 167:439-446 (1986).
Joerger et al., "Cloning, expression, and nucleotide sequence of the *Lactobacillus helvelfcus* 481 gene encoding the bacteriocin helveticin," J. Bacteriol.,172:6339-6347 (1990).
Kamoun et al., "Purification, amino acid sequence and characterization of Bacthuricin F4, a new bacteriocin produced by *Bacillus thuringiensis*," J. of Applied Microbiology, 98:881-888 (2005).
Kampfer et al., "A numerical classification of the genera Streptomyces and Streptoverticillium using miniaturized physiological tests," J. of General Microbiology, 137:1831-1891 (1991).
Kieser et al., "General introduction to actinomycete biology," Practical Streptomyces Genetics, The John Innes Foundation, Norwich, England, p. 19 (2000).
Kimura, "A simple method for estimating evolutionary rates of base substitutions through comparative studies of nucleotide sequences, " J. of Molecular Evolution, 16:111-120 (1980).
Klaenhammer, "Genetics of bacteriocins produced by lactic acid bacteria," FEMS Microbiol. Rev., 12:39-86 (1993).
Kwak et al., "Bald mutants of *Streptomyces* griseus that prematurely undergo key events of sporulation," J. Bacteriol., 178:4643-4650 (1996).
Labeda, "DNA relatedness among strains of the *Streptomyces lavendulae* phenotypic cluster group," Intl. J. Systematic Bacteriol., 43:822-825 (1993).
Labeda, "DNA relatedness among the *Streptomyces fulvissimus* and *Streptomyces giseoviridis* phenotypic cluster groups," Intl. J. Systematic Bacteriol. 48:829-832 (1998).
Labeda, "DNA relatedness among verticil-forming Streptomyces species (formerly Streptoverticillium species)," Int'l. J. Systematic Bacteriol., 46:699-703 (1996).
Laemmli, "Cleavage of structural proteins during the assembly of the head of bacteriophage T4," Nature, 227:680-685 (1970).
Lawlor et al., "Pleiotropic morphological and antibiotic deficiencies result from mutations in a gene encoding a tRNA-like[5] product in *Streptomyces coelicolor* A3(2)," Genes & Development 1:1305-1310 (1987).
Lavermicocca et al., Reduction of olive knot disease by a bacteriocin from *Pseudomonas syringae* pv. Ciccaronei, Appl. Environmental Microbiol., 68:1403-1407 (2002).
Li et al., "*Streptomyces scopiformis* sp. nov., a novel streptomycete with fastigiate spore chains," Intl. J. Systematic and Evolutionary Microbiol., 52:1629-1633 (2002).

(56) References Cited

OTHER PUBLICATIONS

Liu et al., "Enhancement of the chemical and antimicrobial properties of subtilin by site-directed mutagenesis," *J. Biol. Chem.* 267:25078-25085 (1992).

Mazzotta et al., "Nisin induces changes in membrane fatty acid composition of *Listeria monocytogenes* nisin-resistant strains at 10° C. and 30° C.," J. of Applied Microbiology, 82:32-38 (1997).

Messi et al., "Detection and preliminary characterization of a bacteriocin (plantaricin 35d) produced by a *Lactobacillus plantarum* strain," Intl J. Food Microbiol., 64:193-198 (2001).

Neumann et al., "Extracellular proteolytic activation of bacteriolytic peptidoglycan hydrolases of Staphylococcus simulans biovar staphylolyticus," FEMS Microbiology Letters, 110:205-212 (1993).

Nigutova et al., "Production of enterolysin A by rumen Enterococcus fa eca lis strain and occurrence of enlA homologues among ruminal Gram-positive cocci," J. of Applied Microbiology, 102:563-569 (2007).

Nissen-Meyer et al., "Ribosomally synthesized antimicrobial peptides: their function, structure, biogenesis, and mechanism of action," Arch. Microbiol., 167:67-77 (1997).

Oldham et al., "Lysostaphin: use of a recombinant bactericidal enzyme as a mastitis therapeutic," J. Dairy Science, 74:4175-4182 (1991).

Olson et al., "a-proteobacteria cultivated from marine sponges display branching rod morphology," FEMS Microbiology Letters, 211:169-173 (2002).

Rajarathnam et al., "H NMR Studies of Interleukin 8 Analogs: Characterization of the Domains Essential for Function," Biochemistry, 33:6623-6630 (1994).

Riley et al., "Bacteriocins: evolution, ecology, and application," Annual Review of Microbiology, 56:117-137 (2002).

Riley et al., "A survey of Col plasmids in natural isolates of *Escherichia coli* and an investigation into the stability of Col-plasmid lineages," J_ General Microbiol., 138:1345-1352 (1992).

Risoen et al., "Characterization of a broad range antimicrobial substance from *Bacillus cereus*," J. Appl. Microbiol., 96:648-655 (2004).

Roelants et al., "Properties of a bacteriocin-like substance produced by *Streptomyces virginiae*," Antonie Van Leeuwenhoek, 30:45-53 (1964).

Saavedra et al., "Enhancement of the enterocin CRL35 activity by a synthetic peptide derived from the NH2-terminal sequence," Antimicrobial Agents and Chemotherapy, 48:2778-2781 (2004).

Saitou et al., "The neighbor-joining method: a new method for reconstructing phylogenetic trees," Molecular Biology and Evolution, 4:406-425 (1987).

Schnolzer et al., "Constructing proteins by dovetailing unprotected synthetic peptides: backbone-engineered HIV protease," Science, 256:221-225 (1992).

Shah et al., "Lysostaphin-coated catheters eradicate *Staphylococcus aureus* challenge and block surface colonization," Antimicrobial Agents and Chemotherapy, 48:2704-2707 (2004).

Shirling et al., "Methods for characterization of Streptomyces species," Intl J. Systematic Bacteriol., 16:313-340 (1966).

Simmonds et al., "Mode of action of a lysostaphin-like bacteriolytic agent produced by *Streptococcus zooepidemicus* 4881," Appl. Environmental Microbiol., 62:4536-4541(1996).

Simmonds et al., "Cloning and sequence analysis of zooA, a *Streptococci's zooepidemicus* gene encoding a bacteriocin-like inhibitory substance having a domain structure similar to that of lysostaphin," Gene, 189: 255-261 (1997).

Supplementary European Search Report for EP08754501.8 mailed Mar. 10, 2011.

Stern et al., "*Paenibacillus polymyxa* purified bacteriocin to control, *Campylobacter jejuni* in chickens," J. Food Protection, 68:1450-1453 (2005).

Tagg, "Prevention of *Streptococcal pharyngitis* by anti-Streptococcus pyogenes bacteriocin-like inhibitory substances (BLIS) produced by *Streptococcus salivarius*," Indian J. Med. Res., 119(Suppl):13-16 (2004).

Tagg et al., "Bacterial replacement therapy: adapting 'germ warfare' to infection prevention," Trends in Biotechnology, 21(5):217-223 (2003).

Tagg, "Bacteriocins of gram-positive bacteria: an opinion regarding their nature, nomenclature, and numbers," Bacteriocins, Microcins, and Lantabiotics, R. James, C. Lazdunski and F. Pattus (ed), Springer-Verlag, Heidelberg, Germany, pp. 33-36 (1992).

Thomas et al., "Effective use of Nisin to control Bacillus and Clostridium spoilage of a pasteurized mashed potato product," J. Food Protection, 65(10):1580-1585 (2002).

Thompson et al., "Clustal W: improving the sensitivity of progressive multiple sequence alignment through sequence weighting, position-specific gap penalties and weight matrix choice," Nucleic Acids Research, 22:4673-4680 (1994).

Tresner et al., "System of color wheels for streptomycete taxonomy," Appl. Microbiol., 11:335-338 (1963).

Twomey et al., "Protection against *Staphylococcus aureus* mastitis in dairy cows using a bismuth-based teat seal containing the bacteriocin, lacticin 3147," J. Dairy Science, 83:1981-1988 (2000).

Valdes-Stauber et al., "Isolation and characterization of linocin M18, a bacteriocin produced by Brevibacterium linens," Applied and Environmental Microbiology, 60:3809-3814 (1994).

Van Kraaij et al., "Lantibiotics: biosynthesis, mode of action and applications," Natural Product Reports, 16:575-587 (1999).

Waksman et al., "The nomenclature and classification of the actinomycetes," J. Bacteriol., 46:337-341 (1943).

Wayne et al., "Report of the ad hoc committee on reconciliation of approaches to bacterial systematic," Int'l. J. Systematic Bacteriol., 37:463-464 (1987).

Willey et al., "Extracellular complementation of a developmental mutation implicates a small sporulation protein in aerial mycelium formation by S. coelicolor," Cell, 65:641-650 (1991).

Williams et al., "Numerical classification of Streptomyces and related genera," J. of General Microbiology, 129:1743-1813 (1983).

Wu et al., "Lysostaphin disrupts *Staphylococcus aureus* and Staphylococcus epidermidis biofilms on artificial surfaces," Antimicrobial Agents and Chemotherapy, 47(11):3407-3414 (2003).

Zhang et al., "Interstrain inhibition in the sweet potato pathogen *Streptomyces ipomoeae*: purification and characterization of a highly specific bacteriocin and cloning of its structural gene," Appl. Environmental Microbiol., 69:2201-2208 (2003).

Zhou et al., "A dye release assay for determination of lysostaphin activity," Analytical Biochemistry, 171:141-144 (1988).

\* cited by examiner

SEQUENCE LISTING

```
<160> NUMBER OF SEQ ID NOS: 2

<210> SEQ ID NO 1
<211> LENGTH: 15
<212> TYPE: PRT
<213> ORGANISM: Streptomyces scopuliridis

<400> SEQUENCE: 1

Thr Ala Leu Glu Asp Lys Ala Glu Gly Ala Ser Ile Phe Gln Arg
1               5                   10                  15

<210> SEQ ID NO 2
<211> LENGTH: 1376
<212> TYPE: DNA
<213> ORGANISM: Streptomyces scopuliridis

<400> SEQUENCE: 2
gtttgatcct ggctcaggac gaacgctggc ggcgtgctta acacatgcaa gtcgaacgat      60
gaagcctttc ggggtggatt agtggcgaac gggtgagtaa cacgtgggca atctgccctt     120
cactctggga caagccctgg aaacggggtc taataccgga taatacttct gcctgcatgg     180 gcggggggttg aaagctccgg cggtgaagga tgagcccgcg gcctatcagc ttgttggtgg     240
```

```
ggtgatggcc taccaaggcg acgacgggta gccggcctga gagggcgacc ggccacactg    300
ggactgagac acggcccaga ctcctacggg aggcagcagt ggggaatatt gcacaatggg    360
cgaaagcctg atgcagcgac gccgcgtgag ggatgacggc cttcgggttg taaacctctt    420
tcagcaggga agaagcgaga gtgacggtac ctgcagaaga agcgccggct aactacgtgc    480
cagcagccgc ggtaatacgt agggcgcaag cgttgtccgg aattattggg cgtaaagagc    540
tcgtaggcgg cttgtcgcgt cggatgtgaa agcccggggc ttaacccogg gtctgcattc    600 gatacgggca ggctagagtg tggtagggga gatcggaatt cctggtgtag cggtgaaatg    660
cgcagatatc aggaggaaca ccggtggcga aggcggatct ctgggccatt actgacgctg    720
aggagcgaaa gcgtggggag cgaacaggat tagataccct ggtagtccac gccgtaaacg    780
ttgggaacta ggtgttggcg acattccacg tcgtcggtgc cgcagctaac gcattaagtt    840
ccccgcctgg ggagtacggc cgcaaggcta aaactcaaag gaattgacgg gggcccgcac    900
aagcagcgga gcatgtggct taattcgacg caacgcgaag aaccttacca aggcttgaca    960
tacaccggaa acggccagag atggtcgccc ccttgtggtc ggtgtacagg tggtgcatgg    1020
ctgtcgtcag ctcgtgtcgt gagatgttgg gttaagtccc gcaacgagcg caacccttgt    1080
tctgtgttgc cagcatgcct ttcggggtga tggggactca caggagactg ccggggtcaa    1140
ctcggaggaa ggtggggacg acgtcaagtc atcatgcccc ttatgtcttg ggctgcacac    1200
gtgctacaat ggccggtaca atgagctgcg atgccgcgag gcggagcgaa tctcaaaaag    1260
ccggtctcag ttcggattgg ggtctgcaac tcgaccccat gaagtcggag ttgctagtaa    1320
tcgcagatca gcattgctgc ggtgaatacg ttcctgggcc ttgtacacac cgcccg        1376
```

GROWTH ENHANCEMENT AND CONTROL OF BACTERIAL AND FUNGAL PLANT DISEASES WITH *STREPTOMYCES SCOPULIRIDIS*

This application claims benefit of U.S. Provisional Patent Application Ser. No. 61/369,315, filed Jul. 30, 2010.

FIELD OF THE INVENTION

The present invention relates to the enhancement of growth and the control of plant diseases caused by bacterial and fungal pathogens with a newly described species of bacterium, *Streptomyces scopuliridis*.

BACKGROUND OF THE INVENTION

Plants are under almost constant attack by bacterial and fungal pathogens in the environment and economic losses are a frequent consequence of this assault. To avoid or reduce economic loss, synthetic chemical fungicides have been traditionally used to keep the development of disease in check. However, the impact of chemical pesticides on the environment and human health can be harmful; this impact has been well-documented. Improperly used chemical pesticides can contaminate water, air, and soil and can have lasting harmful effects on aquatic life, birds, mammals, and beneficial insects such as bees. Further, pest populations can become resistant to many chemicals requiring the use of higher doses to obtain effective control. As a result, there is increased demand for safe and effective alternatives to chemical pesticides.

Pathogens in the genus *Phytophthora* are known to be causative agents for numerous plant diseases. Sudden oak death, soybean root rot, apple crown and collar rot, and root rots affecting American chestnuts, rhododendron, African violet, and strawberries, are just examples of diseases caused by this group of pathogens. Typically, plant diseases caused by *Phytophthora* are very difficult to control and often lead to the death of the plant. This pathogen is widespread and an economic problem to growers around the world. For example, *Phytophthora infestans* was the infective agent of the potato that caused the Great Irish Famine between 1845 and 1849. Attempts to manage *Phytophthora* spp. with techniques such as rootstock selection and site modification have been mostly unreliable.

Fungi in the genus *Pythium* are commonly called water molds and many *Pythium* spp. are plant pathogens of economic importance in agriculture. *Pythium* damping off is a very common problem in fields and greenhouses where the organism kills newly emerged seedlings (Jarvis, W. R., "Managing Diseases in Greenhouse Crops," APS Press, St. Paul, Minn. (1992)). *Pythium* spp. tend to be very generalistic and unspecific in their host range. They infect a large range of hosts (Owen-Going, T. N., "Etiology and Epidemiology of *Pythium* Root Rot in Bell Pepper (*Capsicum annuum* L.) in Commercial-Scale and Small-Scale Hydroponic Systems," M. Sc. thesis, University of Guelph, Guelph, Ontario (2002)), while *Phytophthora* spp. are generally more host-specific. For this reason, *Pythium* spp. are more devastating to commercial crop production because crop rotation alone will often not eradicate the pathogen (nor will fallowing the field, since *Pythium* spp. are also good saprotrophs, and will survive for long periods of time on decaying plant matter).

*Fusarium* is a large genus of filamentous fungi widely distributed in soil and in association with plants. Most species are harmless saprophytes and are relatively abundant members of the soil microbial community. However, there are a number of important *Fusarium* species that are pathogenic to agricultural crops. For example, some species produce mycotoxins in cereal crops that can affect human and animal health if they enter the food chain. The genus includes a number of economically important plant pathogenic species, including *F. graminearum* that can infect barley, particularly if there is rain late in the season. It is of economic impact to the malting and brewing industries as well as feed barley. *Fusarium* contamination in barley can result in head blight and, in extreme contaminations, the barley can appear pink. *Fusarium graminearum* can also cause root rot and seedling blight. Diseases caused by *Fusarium* spp. can be economically devastating. For example, total losses in the U.S. of barley and wheat crops between 1991 and 1996 from *F. graminearum* are estimated at $3 billion.

*Rhizoctonia* spp. are among the most diverse of plant pathogens, causing root, stem and foliar diseases of many of our most important herbaceous and woody ornamentals. *Rhizoctonia* spp. usually attack plants at the soil line, causing root loss and constriction of the stem which results in girdling and death of the tops. This pathogen can attack leaves as well, and is especially severe when plants are grown close together and kept moist.

*Thielaviopsis* is a small genus of fungi that includes several important agricultural pathogens. The most widespread is *T. basicola*, the causal agent of root rot diseases in crops including cotton and a variety of vegetables. In cotton, *Thielaviopsis* root rot, also known as black root rot, causes necrosis of the roots and stunting of the crop plants.

Powdery mildew is a disease that attacks a wide range of host plants, including cereals and grasses, vegetables, flowers, shrubs, fruit trees, and broad-leaved shade and forest trees. Although powdery mildew appears similar on most host plants, it is caused by a large number of different fungal pathogen genera and species. The disease is characterized by a white or grayish growth on the surface of leaves, stems, flowers, and fruit. It is generally not a fatal disease, but can cause leaf curling and yellowing, stunting of the host plant and defoliation. It is particularly detrimental to ornamental plants, significantly decreasing their value and marketability due to unsightly symptoms.

Downy mildew is a broad category of diseases that can appear on many host plants and is particularly devastating on crucifers, grapes, hops, and many vegetable crops. Symptoms appear as small, green or yellow angular spots on the leaf surface that can spread to the entire plant. Infected plant parts eventually become brown and necrotic and can die.

*Botrytis* blight or gray mold is a fungal disease that infects a wide array of herbaceous annual and perennial plants. There are several species of the fungus *Botrytis* that can cause blights; the most common is *Botrytis cinerea*. *Botrytis* infections are favored by cool, rainy conditions—this disease is particularly damaging when rainy, drizzly weather continues over a period of several days.

Bacterial diseases of plants occur in almost every environment and can be extremely destructive. Their significance as pathogens is based largely on the fact that they can multiply very quickly and produce large numbers of cells in a short period. Bacteria enter through wounds, stomata or other natural openings and can be transmitted in water, through the air, and by contaminated equipment, people, and vehicles.

Bacteria can cause a number of diseases on ornamental and agronomic crops. These include leaf spotting on English ivy, fireblight on apples and pears, crown gall on stone fruits, and wilts in geraniums and cucurbits (cucumbers, squash and melons). Common plant pathogenic bacteria include *Erwinia* spp., *Dickeya* spp., *Pseudomonas* spp., *Xanthomonas* spp., and *Clavibacter michiganensis*. These pathogens may attack plant root systems, foliage, or a combination of both. Disease-free stock plants, resistant cultivars, and sanitation are used to help prevent bacterial diseases. The most common chemical sprays for bacterial diseases contain copper—these help to slow the spread of the disease. In general, chemical sprays for bacterial diseases are less reliable than for most fungal diseases.

The present invention is directed to overcoming these and other deficiencies in the art.

SUMMARY OF THE INVENTION

One aspect of the present invention relates to a method of controlling plant diseases mediated by bacterial or fungal plant pathogens. The method comprises providing *Streptomyces scopuliridis* strain RB72 or an isolated protein or polypeptide comprising the amino acid of SEQ ID NO:1 and applying the *Streptomyces scopuliridis* strain RB72 or an isolated protein or polypeptide comprising the amino acid of SEQ ID NO:1 to plants or plant seeds under conditions effective to treat plant diseases mediated by bacterial or fungal plant pathogens.

Another aspect of the present invention relates to a pathogen-resistant plant or plant seed to which *Streptomyces scopuliridis* strain RB72 or an isolated protein or polypeptide comprising the amino acid of SEQ ID NO:1 is applied.

Yet another aspect of the present invention relates to a planting composition. The planting composition comprises growing media and a *Streptomyces scopuliridis* strain RB72 or an isolated protein or polypeptide comprising the amino acid of SEQ ID NO:1.

Yet a further aspect of the present invention relates to a method of enhancing plant growth. The method comprises providing *Streptomyces scopuliridis* strain RB72 or an isolated protein or polypeptide comprising the amino acid of SEQ ID NO:1 and applying the *Streptomyces scopuliridis* strain RB72 or an isolated protein or polypeptide comprising the amino acid of SEQ ID NO:1 to plants or plant seeds under conditions effective to enhance the growth of the plant or plant seed compared to a plant or plant seed to which the *Streptomyces scopuliridis* strain RB72 or isolated protein or polypeptide was not applied.

Growers and consumers are interested in reducing the use of chemical pesticides in agricultural crops and seek alternative materials for pest management. Effective biological control materials that have a low impact on the environment and non-target organisms can be used as alternatives to, or in a program along with, traditional chemical pesticides. The present invention provides a broad-spectrum control of multiple diseases in agronomic and horticultural crops and a safe alternative to chemical pesticides.

The present invention provides a technology for a new biocontrol agent for plant pathogens. The compositions of the present invention can be used to enhance plant growth and to control both fungal and bacterial pathogens. The compositions can be applied either to the soil or to the foliage.

DETAILED DESCRIPTION OF THE INVENTION

Figure 1:
FIG. 1 is a photograph of a representative Petri dish illustrating in vitro growth inhibition of *Fusarium oxysporum* f. sp. *lycopersici* by *Streptomyces scopuliridis* strain RB72.

One aspect of the present invention relates to a method of controlling plant diseases mediated by bacterial or fungal plant pathogens. The method comprises providing *Streptomyces scopuliridis* strain RB72 or an isolated protein or polypeptide comprising the amino acid of SEQ ID NO:1 and applying the *Streptomyces scopuliridis* strain RB72 or an isolated protein or polypeptide comprising the amino acid of SEQ ID NO:1 to plants or plant seeds under conditions effective to treat plant diseases mediated by bacterial or fungal plant pathogens.

*Streptomyces* is the largest genus of Actinobacter, containing over 500 described species. These bacteria are gram-positive and produce over two-thirds of the commercially available antibiotics derived from natural origins (DAVID A. HOPWOOD, STREPTOMYCES IN NATURE AND MEDICINE: THE ANTIBIOTIC MAKERS (Oxford University Press 2007), which is hereby incorporated by reference in its entirety). Many species of *Streptomyces* are ubiquitous free-living saprophytic soil bacteria, often associated with the plant rhizosphere or decaying organic matter. Because these are competitive environments, *Streptomyces* have evolved a complex secondary metabolism, including the production of numerous antifungal and antibacterial compounds. These include hydrolytic enzymes that allow them to degrade and utilize tough organic materials like lignin and chitin (DAVID A. HOPWOOD, STREPTOMYCES IN NATURE AND MEDICINE: THE ANTIBIOTIC MAKERS (Oxford University Press 2007), which is hereby incorporated by reference in its entirety). Some common antifungal compounds that are produced by *Streptomyces* species include nystatin (from *S. noursei*), amphotericin B (from *S. nodosus*), and natamycin (from *S. natalensis*). Common antibacterial compounds produced include streptomycin (*S. griseus*), neomycin (*S. fradiae*), and tetracycline (*S. rimosus*). Other compounds produced by *Streptomyces* have been found to have antiparasitic and anti-cancer activity (DAVID A. HOPWOOD, STREPTOMYCES IN NATURE AND MEDICINE: THE ANTIBIOTIC MAKERS (Oxford University Press 2007), which is hereby incorporated by reference in its entirety).

A newly discovered species of *Streptomyces*, designated *S. scopuliridis* (originally designated *S. scopuloiridis*; see WO 2009/045234 to Farris et al., which is hereby incorporated by reference in its entirety) strain RB72, was first isolated from a woodland bluff soil from Lynn, Ala. (Farris et al., "*Streptomyces scopuliridis* sp. nov., A Bacterocin-Producing Soil Streptomycete," *Int. J. Syst. Eva Microbiol.* (2010), which is hereby incorporated by reference in its entirety). Strain RB72 produces a 27 kDa bacteriocin-like enzyme (BLIS RB72) that has a broad spectrum of bacteriolytic activity against both gram-positive and gram-negative bacteria. Most notably, the spectrum of activity includes the important human pathogens *Streptococcus pyogenes*, *Staphylococcus aureus*, *Escherichia coli*, and *Klebsiella pneumoniae* as well as other members of the genus *Streptomyces*, while the producer strain (RB72) remains immune to the lytic effects (WO 2009/045234 to Farris et al., which is hereby incorporated by reference in its entirety). In addition to activity against human pathogens, activity against plant pathogenic bacteria and fungi has been observed using RB72, indicating that there is an important use for RB72 as a biological control organism. This organism is described in WO 2009/045234 to Farris et al., which is hereby incorporated by reference in its entirety.

Biological control (biocontrol) of plant pathogens is becoming an increasingly essential component in plant disease management. Many microorganisms are known to control various plant pathogens using multiple modes of activity, thereby reducing the risk of developing resistant pest populations. Currently, there are numerous microbial-based biocontrol products commercially available, including products containing *Trichoderma* spp., *Bacillus* spp., and *Streptomyces* spp. Each biocontrol organism can work through various modes of activity, including antibiosis, mycoparasitism, competitive exclusion, secondary metabolism, or a combination of factors. *Streptomyces* have been previously described as rhizosphere-colonizing bacteria (Miller et al., "The Dynamics of *Actinomycetes* and Fluorescent *Pseudomonads* in Wheat Rhizoplane and Rhizosphere," *Symbiosis* 9:389-391 (1990), which is hereby incorporated by reference in its entirety), in vitro siderophore producers (DAVID A. HOPWOOD, STREPTOMYCES IN NATURE AND MEDICINE: THE ANTIBIOTIC MAKERS (Oxford University Press 2007), which is hereby incorporated by reference in its entirety), and secondary metabolite (both antifungal and antibacterial) producers (Rothrock et al., "Role of Antibiosis in Antagonism of *Streptomyces hygroscopicus* var. *geldanus* to *Rhizoctonia solani* in Soil," *Can. J. Microbiol.* 30:1440-1447 (1984), which is hereby incorporated by reference in its entirety). In addition, *Streptomyces* synthesize an array of bio-degradative enzymes, including chitinases (Blaak et al., "Characteristics of an Exochitinase from *Streptomyces olivaceoviridis*, its Corresponding Gene, Putative Protein Domains and Relationship to other Chitinases," *Eur. J. Biochem.* 214:659-669 (1993); Gupta et al., "Chitinase Production by *Streptomyces viridificans*: Its Potential in Fungal Cell Wall Lysis," *J. Appl. Bacteriol.* 78:378-383 (1995), which are hereby incorporated by reference in their entirety), glucanases (Thomas et al., "Cloning of Clustered *S. viridosporus* T7A Lignocellulose Catabolism Genes Encoding Peroxidase and Endoglucanase and their Extracellular Expression in *Pichia pastoris*," *Can. J. Microbiol.* 44:364-372 (1998); Trejo-Estrada et al., "Antibiotics and Enzymes Produced by the Biological Control Agent *Streptomyces violaceusniger* YCED-9," *J. Ind. Microbiol. Technol.* 21:81-90 (1998), which are hereby incorporated by reference in their entirety), peroxidases (Ramachandra et al., "Characterization of an Extracellular Lignin Peroxidase of the Lignocellulolytic Actinomycete *Streptomyces viridosporus*," *Appl. Environ. Microbiol.* 54:3057-3063 (1988), which is hereby incorporated by reference in its entirety), and other enzymes possibly involved in mycoparasitic activity.

*Streptomyces scopuliridis* strain RB72 exhibits a range of chemotaxonomic and phenotypic characters typical of the members of the genus *Streptomyces*, as noted in WO 2009/045234 to Farris et al., which is hereby incorporated by reference in its entirety. Strain RB72 forms an extensively branched substrate mycelium and aerial hyphae on several standard growth media. *Streptomyces scopuliridis* strain RB72 produces white aerial hyphae with no spores and a golden brown substrate mycelium on all standard morphological media tested with the exception of International *Streptomyces* Project medium 2 (ISP2), on which the extent of the aerial hyphae formation is reduced and the substrate mycelium does not produce pigment. Sporulation of the aerial hyphae is not detected after prolonged growth periods, and the aerial hyphae remain white in color, typical of other *Streptomyces* strains that do not sporulate. These results suggest a deficiency in the whi pathway of the organism.

In one embodiment the *Streptomyces scopuliridis* is deposited under ARS Culture Collection No. NRRL B-24574 and under DSMZ general collection accession number DSM 41917. In one embodiment, the isolated protein or polypeptide is the *Streptomyces* sp. strain RB72 bacteriocin BLIS RB72.

In another embodiment of the present invention, the *Streptomyces scopuliridis* strain RB72 bacterium comprises a 16S rRNA nucleic acid sequence that is deposited under GenBank Accession No. EF657884. In yet another embodiment, the bacterium comprises a 16S rRNA nucleic acid identified as SEQ ID NO:2 as follows:

```
gtttgatcct ggctcaggac gaacgctggc ggcgtgctta acacatgcaa gtcgaacgat gaagcctttc ggggtggatt agtggcgaac gggtgagtaa cacgtgggca atctgccctt cactctggga caagccctgg aaacggggtc taataccgga taatacttct gcctgcatgg gcggggttg aaagctccgg cggtgaagga tgagcccgcg gcctatcagc ttgttggtgg ggtgatggcc taccaaggcg acgacgggta gccggcctga gagggcgacc ggccacactg ggactgagac acggcccaga ctcctacggg aggcagcagt ggggaatatt gcacaatggg cgaaagcctg atgcagcgac gccgcgtgag ggatgacggc cttcgggttg taaacctctt tcagcaggga agaagcgaga gtgacggtac ctgcagaaga agcgccggct aactacgtgc cagcagccgc ggtaatacgt agggcgcaag cgttgtccgg aattattggg cgtaaagagc
```

```
                        -continued
tcgtaggcgg cttgtcgcgt cggatgtgaa agcccggggc ttaaccccgg gtctgcattc gatacgggca ggctagagtg tggtagggga gatcggaatt cctggtgtag cggtgaaatg cgcagatatc aggaggaaca ccggtggcga aggcggatct ctgggccatt actgacgctg aggagcgaaa gcgtggggag cgaacaggat tagatatcct ggtagtccac gccgtaaacg ttgggaacta ggtgttggcg acattccacg tcgtcggtgc cgcagctaac gcattaagtt ccccgcctgg ggagtacggc cgcaaggcta aaactcaaag gaattgacgg gggcccgcac aagcagcgga gcatgtggct taattcgacg caacgcgaag aaccttacca aggcttgaca tacaccggaa acggccagag atggtcgccc ccttgtggtc ggtgtacagg tggtgcatgg ctgtcgtcag ctcgtgtcgt gagatgttgg gttaagtccc gcaacgagcg caacccttgt tctgtgttgc cagcatgcct ttcggggtga tggggactca caggagactg ccggggtcaa ctcggaggaa ggtggggacg acgtcaagtc atcatgcccc ttatgtcttg ggctgcacac gtgctacaat ggccggtaca atgagctgcg atgccgcgag gcggagcgaa tctcaaaaag ccggtctcag ttcggattgg ggtctgcaac tcgacccccat gaagtcggag ttgctagtaa tcgcagatca gcattgctgc ggtgaatacg ttcctgggcc ttgtacacac cgcccg
```

In yet another embodiment, the bacterium produces a bacteriocin comprising a polypeptide comprising a 15 amino acid sequence of Thr Ala Leu Glu Asp Lys Ala Glu Gly Ala Ser Ile Phe Gln Arg (SEQ ID NO:1), where the polypeptide has a weight of about 27 kDa as visualized by SDS-PAGE.

Each of the disclosed polypeptides, and fragments thereof, can have one or more conservative amino acid substitutions. These conservative substitutions are such that a naturally occurring amino acid is replaced by one having similar properties and do not alter the function of the polypeptide. Such substitutions are outlined in WO 2009/045234 to Farris et al., which is hereby incorporated by reference in its entirety. In particular, these substitutions are exemplified in Table 1, as follows:

TABLE 1

Conservative Amino Acid Substitutions

| Original Residue | Exemplary Substitutions |
|---|---|
| Arg | Lys |
| Asn | Gln |
| Asp | Glu |
| Cys | Ser |
| Gln | Asn |
| Glu | Asp |
| Gly | Pro |
| His | Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Thus, it is understood that, where desired, modifications and changes may be made in the nucleic acid encoding the polypeptide of the present invention and/or in the amino acid sequence of that polypeptide. However, with these changes, a polypeptide having like or otherwise desirable characteristics can be obtained. Such changes may occur in natural isolates or may be synthetically introduced using site-specific mutagenesis, the procedures for which, such as mis-match polymerase chain reaction ("PCR"), are well known in the art. For example, certain amino acids may be substituted for other amino acids in a polypeptide without appreciable loss of functional activity. It is thus contemplated that various changes may be made in the amino acid sequence of the polypeptides of the present invention (or underlying nucleic acid sequence) without appreciable loss of biological utility or activity and possibly with an increase in such utility or activity.

It will be understood that such polypeptide or nucleotide sequence variations may be measured in terms of similarity or homology to the disclosed sequences. In one embodiment, variants of nucleic acid and/or polypeptide sequences disclosed herein include those with at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, 98.87, or 99 percent similarity or homology to SEQ ID NO:1 and/or SEQ ID NO:2. Those of skill in the art will readily appreciate how to determine such similarity or homology.

The methods of the present invention are to be used to control plant disease that is mediated by a bacterial plant pathogen, a fungal plant pathogen, or both.

In certain embodiments, the plant disease is mediated by a fungal plant pathogen. Plant diseases mediated by a fungal plant pathogen that are treatable in accordance with the present invention, can result from *Pythium, Fusarium, Rhizoctonia, Thielaviopsis, Phytophthora*, powdery mildew, downy mildew, *Botrytis*, and/or *Sclerotium* infection.

Plant diseases that are mediated by a *Phytophthora* species, which are treatable in accordance with the present invention, can result from *Phytophthora cactorum, Phytophthora cinnamomi, Phytophthora citricola, Phytophthora citrophthora, Phytophthora cryptogea, Phytophthora drecshsleri, Phytophthora infestans*, and *Phytophthora nicotianae* infection.

Plant diseases that are mediated by a *Pythium* species, which are treatable in accordance with the present invention, can result from *Pythium aphanidermatum, Pythium irregulare*, and/or *Pythium ultimum* infection.

Plant diseases that are mediated by a *Fusarium* species, which are treatable in accordance with the present invention, can result from *Fusarium oxysporum* infection.

Plant diseases that are mediated by a *Rhizoctonia* species, which are treatable in accordance with the present invention, can result from *Rhizoctonia solani* infection.

Plant diseases that are mediated by a *Thielaviopsis* species, which are treatable in accordance with the present invention, can result from *Thielaviopsis basicola* infection.

Plant diseases that are mediated by a *Sclerotium* species, which are treatable in accordance with the present invention, can result from *Sclerotium rolfsii* infection.

Plant diseases known as powdery mildew, which are treatable in accordance with the present invention, can result from infection caused by species in the genera *Erysiphe, Leveillula, Microsphaera, Podosphaera, Oidium, Phyllactinia, Sphaerotheca*, and *Uncinula*. Other organisms mediating powdery mildew, which are treatable in accordance with the present invention, will be known to those of skill in the art. See R. KENNETH HORST, WESTCOTT'S PLANT DISEASE HANDBOOK (Kluwer Academic Publishers 6$^{th}$ edition 2001), which is hereby incorporated by reference in its entirety).

Plant diseases known as downy mildew, which are treatable in accordance with the present invention, can result from infection caused by several species and genera in the family Peronosporaceae. For example, downy mildew can result from infection by species in the genera *Basidiophora, Bremia, Peronosclerospora, Peronospora, Plasmopara, Pseudoperonospora*, and *Sclerospora*. Other organisms mediating downy mildew, which are treatable in accordance with the present invention, will be known to those of skill in the art. See R. KENNETH HORST, WESTCOTT'S PLANT DISEASE HANDBOOK (Kluwer Academic Publishers 6$^{th}$ edition 2001), which is hereby incorporated by reference in its entirety).

Plant diseases that are mediated by a *Botrytis* species, which are treatable in accordance with the present invention, can result from *Botrytis cinerea, Botrytis fabae, Botrytis ricini*, or *Botrytis elliptica* infection. Other *Botrytis* species mediating plant diseases, which are treatable in accordance with the present invention, will be known to those of skill in the art. See R. KENNETH HORST, WESTCOTT'S PLANT DISEASE HANDBOOK (Kluwer Academic Publishers 6$^{th}$ edition 2001), which is hereby incorporated by reference in its entirety).

In certain embodiments, the plant disease is mediated by a bacterial plant pathogen. In particular, the plant disease may be mediated by a bacterial plant pathogen including *Erwinia, Pseudomonas, Xanthomonas, Clavibacter*, and/or *Dickeya*.

Plant diseases that are mediated by an *Erwinia* species, which are treatable in accordance with the present invention, can result from strains of *Erwinia amylovora, E. aphidicola, E. billingiae, E. mallotivora E. papayae, E. persicina, E. psidii, E. pyrifoliae, E. rhapontici, E. toletana*, and *E. tracheiphila*. Other *Erwinia* species mediating plant diseases, which are treatable in accordance with the present invention, will be known to those of skill in the art.

Plant diseases that are mediated by a *Dickeya* species, which are treatable in accordance with the present invention, can result from strains of *Dickeya chrysanthemi, D. dadantii*, and *D. solani*. Other *Dickeya* species mediating plant diseases, which are treatable in accordance with the present invention, will be known to those of skill in the art.

Plant diseases that are mediated by a *Pseudomonas* species, which are treatable in accordance with the present invention, can result from pathovars of *Pseudomonas amygdale, P. avellanae, P. caricapapayae, P. cichorii, P. coronafaciens, P. ficuserectae, P. helianthi, P. meliae, P. savastanoi, P. syringae, P. tomato*, and *P. viridiflava*. Other *Pseudomonas* species mediating plant diseases, which are treatable in accordance with the present invention, will be known to those of skill in the art.

Plant diseases that are mediated by a *Xanthomonas* species, which are treatable in accordance with the present invention, can result from pathovars of *Xanthomonas albilineans, X. alfalfae, X. ampelina, X. arboricola, X. axonopodis, X. boreopolis, X. badrii, X. bromi, X. campestris, X. cassayae, X. citri, X. codiaei, X. cucurbitae, X. cyanopsidis, X. cynarae, X. euvesicatoria, X. fragariae, X. gardneri, X. holcicola, X. hortorum, X. hyacinthi, X. malvacearum, X. maltophilia, X. manihotis, X. melonis, X. oryzae, X. papavericola, X. perforans, X. phaseoli, X. pisi, X. populi, X. sacchari, X. theicola, X. translucens, X. vasicola, X. vesicatoria*. Other *Xanthomonas* species mediating plant diseases, which are treatable in accordance with the present invention, will be known to those of skill in the art.

Plant diseases that are mediated by a *Clavibacter* species, which are treatable in accordance with the present invention, can result from *Clavibacter michiganensis* infection. Plant diseases that are mediated by a *Clavibacter michiganensis* subspecies, which are treatable in accordance with the present invention, can result from *Clavibacter michiganensis* subsp. *insidiosus* and/or *Clavibacter michiganensis* subsp. *michiganensis* infection. Other *Clavibacter* species mediating plant diseases, which are treatable in accordance with the present invention, will be known to those of skill in the art.

Plants treated in accordance with the present invention include any plant susceptible to fungal or plant pathogen. For example, plants treated in accordance with the present invention include, but are not limited to, agronomic row or other field crops that include buckwheat, beans (soybean, snap, dry), corn (grain, seed, sweet corn, silage, popcorn, high oil), cotton, canola, peas (dry, succulent), peanuts, safflower, and sunflower; alfalfa hay and forage crops that include alfalfa, clover, vetch, and trefoil; berries and small fruits that include blackberries, blueberries, currants, elderberries, gooseberries, huckleberries, loganberries, raspberries, strawberries, grapes, bulb crops: garlic, leeks, onions, shallots, and ornamental bulbs; citrus fruits that include citrus hybrids, grapefruit, kumquat, limes, oranges, and pummelos; cucurbit vegetables that include cucumbers, melons, gourds, pumpkins, squash, and flowers; bedding plants and ornamentals; fruiting vegetables that include eggplant, sweet and hot peppers, tomatillos, tomatoes, herbs, spices, and mints; hydroponic crops that include cucumbers, tomatoes, and lettuce; herbs and spices; leafy vegetables and cole crops that include arugula, celery, chervil, endive, fennel, lettuce (head and leaf), parsley, radicchio, rhubarb, spinach, Swiss chard, broccoli, Brussels sprouts, cabbage, cauliflower, collards, kale, kohlrabi, mustard greens, and asparagus; legume vegetable and field crops that include snap and dry beans, lentils, succulent and dry peas, peanuts, and soybeans; pome fruit that include pears, quince; root crops that include beets, sugarbeets, red beets, carrots, celeriac, chicory, horseradish, parsnip, radish rutabaga, salsify, turnips; shadehouse and other nursery crops that include deciduous trees (maple, oak), ornamentals, grapes, citrus, pine; small grains that include rye, wheat, sorghum, and millet; stone fruits that include apricots, cherries, nectarines, peaches, plums, prunes, tree nuts: almonds, beech nuts, Brazil nuts, butternuts, cashews, chestnuts, filberts, hickory nuts, macadamia nuts, pecans, pistachios, and walnuts; tuber crops that include potatoes, sweet potatoes, yams, artichoke, cassaya, and ginger. Other examples include those grasses associated with turfgrass, turf, sports fields, parks, established and new preparation of golf course tees, greens, fairways and roughs, seed production and sod production. Plants that may be treated also include petunia, pelargonium, poinsettia, chrysanthemum, carnation, and zinnia.

To control target pathogens, plants may be cultivated within the effective area of the *Streptomyces scopuliridis* strain RB72, an isolated protein or polypeptide comprising the amino acid of SEQ ID NO:1, or mixtures thereof. In certain embodiments, seeds can be planted in soil mixed with the *Streptomyces scopuliridis* strain RB72 or an isolated protein or polypeptide comprising the amino acid of SEQ ID NO:1. In another embodiment, the *Streptomyces scopuliridis* strain RB72 and/or an isolated protein or polypeptide comprising the amino acid of SEQ ID NO:1 is applied to a growing plant. A growing plant is provided in an environment susceptible to a plant disease mediated by bacterial or fungal plant pathogen and the *Streptomyces scopuliridis* strain RB72 and/or an isolated protein or polypeptide is applied directly or indirectly (e.g., through the soil) to the growing plant.

Several other methods of introducing the *Streptomyces scopuliridis* strain RB72 or isolated protein or polypeptide to the plant would be equally effective. For example, the *Streptomyces scopuliridis* strain RB72 or isolated protein or polypeptide could be fermented, formulated, or packaged. Then the *Streptomyces scopuliridis* strain RB72 or isolated protein or polypeptide can be applied to the plant seed by dry or wet formulation and application to the seed. Alternatively, the *Streptomyces scopuliridis* strain RB72 or isolated protein or polypeptide could be produced in an in-furrow formulation, wet or dry, which can be applied to the soil where the plant is to be grown. The *Streptomyces scopuliridis* strain RB72 or isolated protein or polypeptide can even be applied as a spray, directed either in furrow during planting, to the soil surface after planting or by foliar application. They may also be applied as a drench to potted plants and may be incorporated into a growing medium. The *Streptomyces scopuliridis* strain RB72 or isolated protein or polypeptide may be placed by some means in the soil environment adjacent to the growing plant. The plant foliage may also be treated by wet or dry application. The *Streptomyces scopuliridis* strain RB72 or isolated protein or polypeptide may be applied to the foliage by high or low pressure spray application. Foliar application can also be carried out by coating, immersion, or dusting. By "target pathogen" is meant the pathogen or pathogens, known or unknown, which threatens the plant.

The *Streptomyces scopuliridis* strain RB72 and/or an isolated protein or polypeptide comprising the amino acid of SEQ ID NO:1 may be provided and applied in the form of a biocontrol composition in any of the embodiments of the present invention.

The protein or polypeptide according to the present invention may be recombinantly produced for use in accordance with the present invention using techniques known in the art. For instance, well known molecular cloning techniques as described in Sambrook et al., *Molecular Cloning: A Laboratory Manual*, Cold Springs Laboratory, Cold Springs Harbor, N.Y. (2001 and preceding editions), and Ausubel et al. (ed.), *Current Protocols in Molecular Biology*, John Wiley & Sons (New York, N.Y.) (1999 and preceding editions), which are hereby incorporated by reference in their entirety, may be used to produce the polypeptide of the present invention. The proteins and polypeptides of the present invention can also be synthesized in a cell-free protein synthesis system. The above expression vector DNA is transcribed in vitro, and the resultant mRNA is added to a cell-free translation system to synthesize the protein. Specifically, the cell-free translation system is prepared from an extract of a eukaryotic cell or a bacterial cell, or a portion thereof. Such cell-free translation systems include those prepared from a rabbit reticulocyte, from a wheat germ, and from *E. coli* S30 extract. Chemical synthesis can also be used to make suitable proteins or polypeptides. Such a synthesis is carried out using known amino acid sequences for the proteins and polypeptides of the present invention. These proteins and polypeptides can then be separated by conventional procedures (e.g., chromatography, SDS-PAGE) and used in the methods of the present invention.

The proteins and polypeptides of the present invention may be purified by methods that will be apparent to one of skill in the art.

The applying step of the *Streptomyces scopuliridis* strain RB72 and/or an isolated protein or polypeptide may also be carried out by broadcast application, liquid or dry in-furrow application, direct incorporation into soils or greenhouse planting mixes, dust or planter box treatments, or direct seed treatment.

The present invention can include a carrier. Suitable carriers include water, aqueous solution, slurries, granules, or powders.

Other additives suitable for inclusion in the composition are chemical fertilizer, insecticide, fungicide, nematicide, organic fertilizer, bioinsecticide, biofungicide, bionematicide, agricultural or horticultural adjuvants including stickers, spreaders, surfactants, dispersants, humectants and U.V. protectants, or mixtures thereof.

Another aspect of the present invention relates to a pathogen-resistant plant or plant seed to which *Streptomyces scopuliridis* strain RB72 or an isolated protein or polypeptide comprising the amino acid of SEQ ID NO:1 is applied. This aspect of the invention also includes plants grown from plant seed to which *Streptomyces scopuliridis* strain RB72 or an isolated protein or polypeptide comprising the amino acid of SEQ ID NO:1 is applied.

Yet another aspect of the present invention relates to a planting composition. The planting composition comprises growing media and a *Streptomyces scopuliridis* strain RB72 or an isolated protein or polypeptide comprising the amino acid of SEQ ID NO:1.

Growing media may include any agriculturally acceptable growing media. Growing media may include, for example, soil, sand, compost, peat, rice hulls, coir, cocopeat, soilless growing media containing organic and/or inorganic ingredients, artificial plant-growth substrates, polymer-based growth matrices, hydroponic nutrient and growth solutions, organic soil amendments, and combinations or mixtures thereof.

Another aspect of the present invention relates to a method of enhancing plant growth. This involves providing a the *Streptomyces scopuliridis* strain RB72 or isolated protein or polypeptide comprising the amino acid of SEQ ID NO:1. The *Streptomyces scopuliridis* strain RB72 or isolated protein or polypeptide is applied to plants under conditions effective to enhance plant growth, as compared to plants where they were not applied.

This aspect of the present invention is carried out with substantially the same materials and procedures described above with reference to the method of controlling diseases. It is directed to affecting any form of plant growth enhancement or promotion. This can occur as early as when plant growth begins from seeds or later in the life of a plant. For example, plant growth according to the present invention encompasses greater yield, increased quantity of seeds produced, increased percentage of seeds germinated, increased plant size, greater biomass, more and bigger fruit, earlier fruit coloration, and earlier fruit and plant maturation. As a result, the present invention provides significant economic benefit to growers. For example, early germination and early maturation permit crops to be grown in areas where short growing seasons would otherwise preclude their growth in that locale. Increased percentage of seed germination results in improved crop stands and more efficient seed use. Greater yield, increased size, and enhanced biomass production allow greater revenue generation from a given plot of land. It is thus apparent that the present invention constitutes a significant advance in agricultural efficiency.

EXAMPLES

The examples that follow are given for illustrative purposes and are not meant to limit the invention described herein. These examples are given to demonstrate the biocontrol activity of *Streptomyces scopuliridis* strain RB72 on a variety of agronomically important fungal and bacterial plant pathogens, as well as growth enhancement effects of application of *Streptomyces scopuliridis* strain RB72 to plants.

I. In Vitro Inhibition of Bacterial and Fungal Plant Pathogens
Materials and Methods for Examples 1-13
Fungal and Bacterial Growth Conditions and Methods for In Vitro Inhibition and Bacterial Cell Lysis Studies All fungal and bacterial growth media were prepared using distilled water and sterilized by autoclaving prior to use. All samples were handled using standard aseptic techniques to maintain purity and alleviate contamination.

YDC Media has with the following make-up per 1 L: Yeast extract (Fisher Scientific, 10 g), Calcium carbonate (Sigma, 20 g), D-glucose (dextrose) (Fisher Scientific, 20 g), Agar (Fisher Scientific, 17 g). PDA was used with the following make-up per 1 L: Potato dextrose agar (Fisher Scientific, 39 g), Agar (Fisher Scientific, 3 g). Nutrient broth has the following make-up per 1 L: Nutrient broth (Fisher Scientific, 8 g). Nutrient agar+0.4% dextrose has with the following make-up per 1 L: Nutrient broth (Fisher Scientific, 8 g), Agar (Fisher Scientific, 17 g), Dextrose (Fisher Scientific, 4 g). SYZ liquid broth has the following make-up per 1 L: Soluble starch (Fisher Scientific, 15 g), Yeast extract (Fisher Scientific, 2 g), NZ-Amine (Amresco, 4 g), Dextrose (Fisher Scientific, 2 g).

Phytopathogenic fungal and bacterial strains *Pythium ultimum*, *Pythium irregulare*, *Pythium aphanidermatum*, *Phytophthora nicotianae*, *Rhizoctonia solani*, *Fusarium oxysporum* f. sp. *lycopersici*, *Xanthomonas campestris*, *Pseudomonas syringae*, *Erwinia amylovora*, *Clavibacter michiganensis* subsp. *insidiosus*, and *Clavibacter michiganensis* subsp. *michiganensis* were obtained from Cornell University, Department of Plant Pathology and Plant-Microbe Biology, Ithaca N.Y. Pathogens and RB72 were maintained on YDC or PDA media and grown at 27° C.

For the fungal in vitro inhibition studies, the following methods were used: *S. scopuliridis* strain RB72 was streaked down the center of an YDC media plate and allowed to incubate in a grow room at 27° C. for 4 days. Agar plugs collected from a Petri plate containing actively growing pathogen cultures were transplanted to either side of the RB72 streak. This was repeated for a total of 5 replicate plates. Control plates containing the pathogen alone were used to compare fungal growth. Plates were incubated at 27° C. for 72 hours, or until the pathogen hyphae had reached the outer edge of the plate.

For the bacterial in vitro inhibition studies, the following methods were used: *S. scopuliridis* strain RB72 was streaked down the center of a YDC media plate and allowed to incubate in a grow room at 27° C. for 4 days. Bacterial colonies were streaked across the plate in the opposite direction (horizontal streaks) at the top, center, and bottom of the plate. This was repeated on a total of 5 replicate plates. Growth on control plates was compared to growth on plates containing the pathogen alone.

For the bacterial heat-killed cell lysis assay, the following methods were used: bacterial phytopathogen strains *Xanthomonas campestris*, *Pseudomonas syringae*, *Erwinia amylovora*, *Clavibacter michiganensis* subsp. *michiganensis*, and *Clavibacter michiganensis* subsp. *insidiosus* were grown up in liquid culture in either nutrient broth or SYZ liquid broth to turbidity (ranged from 3-7 days). Flasks containing cultures were autoclaved and the heat-killed cells were pelleted via centrifugation. Cell pellets were washed once with DI water and resuspended into small amounts of boiled nutrient agar containing 0.4% dextrose. Agars containing heat-killed pathogens were autoclaved and poured into Petri plates. Plates were inoculated with an actively growing colony of *Streptomyces scopuliridis* strain RB72, and grown at room temperature for three weeks. Plates were observed for a zone of lysis, or a clearing of heat killed cells in the agar.

Example 1

Inhibition of *Fusarium oxysporum* f. sp. *lycopersici*

This example gives an illustration of the inhibitory activity of *Streptomyces scopuliridis* strain RB72, according to the present invention, on the fungal plant pathogen, *Fusarium oxysporum* f. sp. *lycopersici*.

As set forth in Table 2, growth inhibition of *F. oxysporum* f. sp. *lycopersici* was 62.07%. FIG. 1 is a photograph of a representative Petri dish showing growth inhibition of *F. oxysporum* f. sp. *lycopersici*.

TABLE 2

Quantitative Growth Inhibition of Phytopathogens by *Streptomyces scopuliridis* Strain RB72.

| Phytopathogen | Growth Inhibition by RB72 |
| --- | --- |
| *Fusarium oxysporum* f.sp. *lycopersici* | 62.07% |
| *Rhizoctonia solani* | 83.92% |
| *Pythium ultimum* | 67.65% |
| *Pythium irregulare* | 68.02% |
| *Pythium aphanidermatum* | 68.84% |
| *Phytophthora nicotianae* | 73.44% |
| *Clavibacter michiganensis* subsp. *insidiosus* | ++ |
| *Clavibacter michiganensis* subsp. *michiganensis* | +++ |

+++ Very strong growth inhibition,
++ Strong growth inhibition,
+ Moderate growth inhibition Growth inhibition for fungal phytopathogens is defined as a percentage of growth inhibition compared to a control plate. Data were taken from five replicate plates for each fungal phytopathogen. For bacterial phytopathogens, growth inhibition was determined as either retarded or prevented in the area of the plate colonized by RB72. Data were taken from five replicate plates for each bacterial phytopathogen.

Example 2

Inhibition of *Rhizoctonia solani*

This example gives an illustration of the inhibitory activity of *Streptomyces scopuliridis* strain RB72, according to the present invention, on the fungal plant pathogen, *Rhizoctonia solani*.

Figure 2:
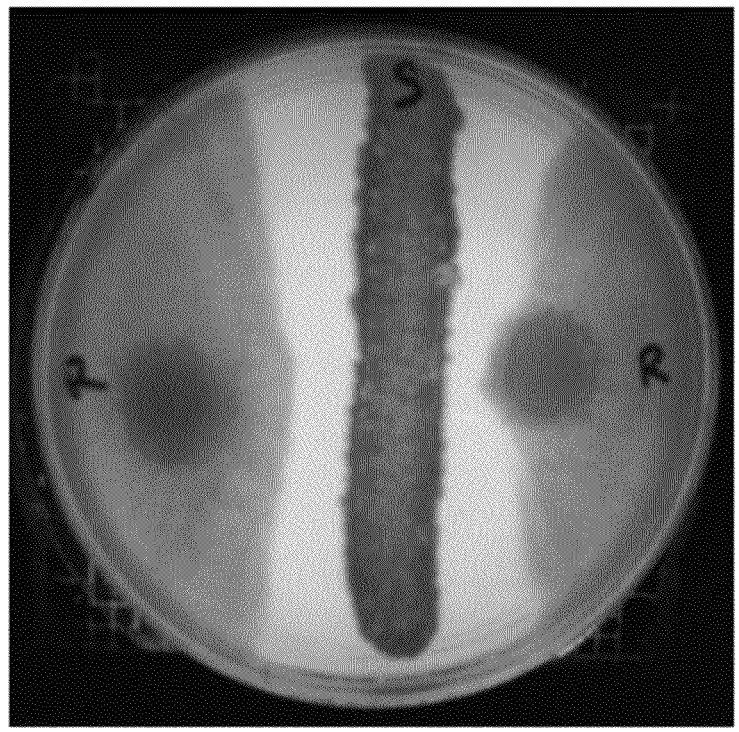
FIG. 2 is a photograph of a representative Petri dish illustrating in vitro growth inhibition of *Rhizoctonia solani* by *Streptomyces scopuliridis* strain RB72.

As set forth in Table 2, growth inhibition of *R. solani* was rated as 83.92%. FIG. 2 is a photograph of a representative Petri dish showing growth inhibition of *Rhizoctonia solani*.

Example 3

Inhibition of *Pythium ultimum*

This example gives an illustration of the inhibitory activity of *Streptomyces scopuliridis* strain RB72, according to the present invention, on the fungal plant pathogen, *Pythium ultimum*.

Figure 3:
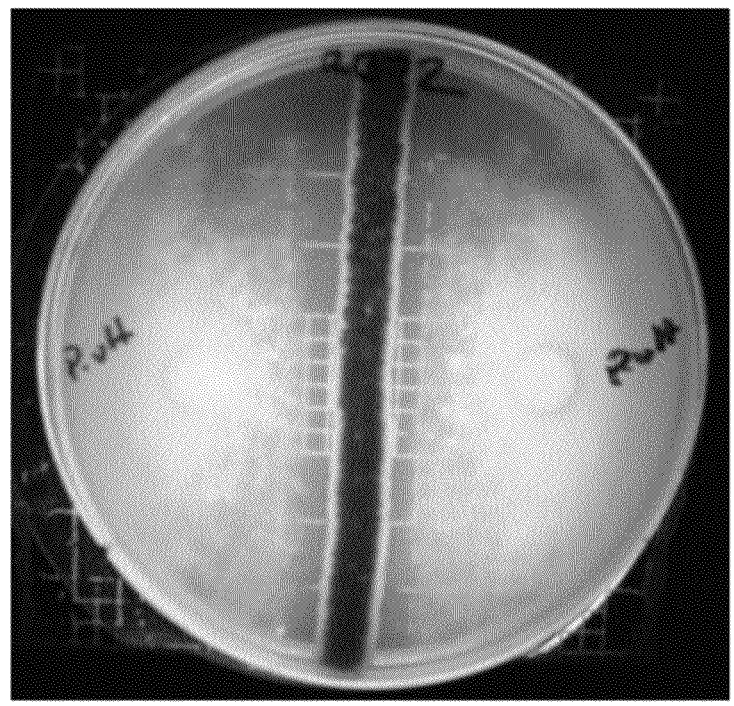
FIG. 3 is a photograph of a representative Petri dish illustrating in vitro growth inhibition of *Pythium ultimum* by *Streptomyces scopuliridis* strain RB72.

As set forth in Table 2, growth inhibition of *P. ultimum* was rated as 67.65%. FIG. 3 is a photograph of a representative Petri dish showing growth inhibition of *Pythium ultimum*.

Example 4

Inhibition of *Pythium irregulare*

This example gives an illustration of the inhibitory activity of *Streptomyces scopuliridis* strain RB72, according to the present invention, on the fungal plant pathogen, *Pythium irregulare*.

Figure 4:
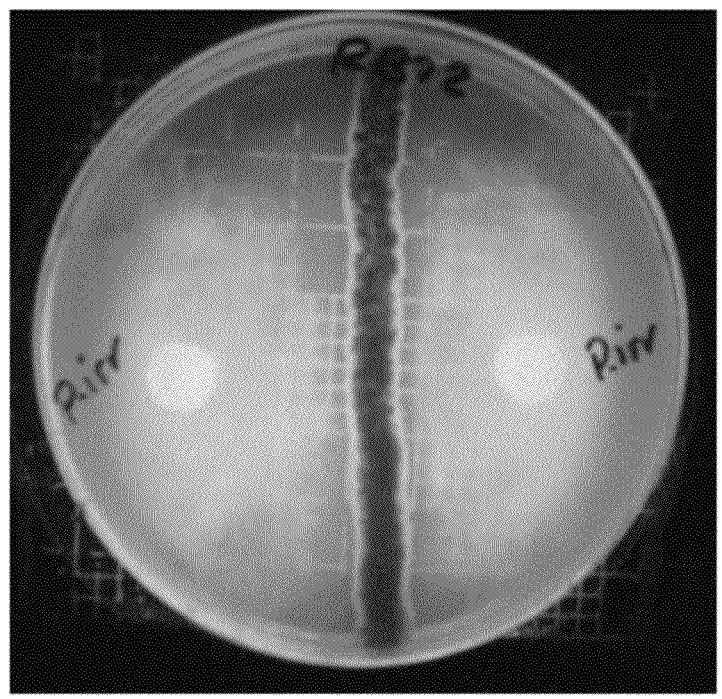
FIG. 4 is a photograph of a representative Petri dish illustrating in vitro growth inhibition of *Pythium irregulare* by *Streptomyces scopuliridis* strain RB72.

As set forth in Table 2, growth inhibition of *P. irregulare* was rated as 68.02%. FIG. 4 is a photograph of a representative Petri dish showing growth inhibition of *Pythium irregulare*.

Example 5

Inhibition of *Pythium aphanidermatum*

This example gives an illustration of the inhibitory activity of *Streptomyces scopuliridis* strain RB72, according to the present invention, on the fungal plant pathogen, *Pythium aphanidermatum*.

Figure 5:
FIG. 5 is a photograph of a representative Petri dish illustrating in vitro growth inhibition of *Pythium aphanidermatum* by *Streptomyces scopuliridis* strain RB72.

As set forth in Table 2, growth inhibition of *P. aphanidermatum* was rated as 68.84%. FIG. 5 is a photograph of a representative Petri dish showing growth inhibition of *Pythium aphanidermatum*.

Example 6

Inhibition of *Phytophthora nicotianae*

This example gives an illustration of the inhibitory activity of *Streptomyces scopuliridis* strain RB72, according to the present invention, on the fungal plant pathogen, *Phytophthora nicotianae*.

Figure 6:
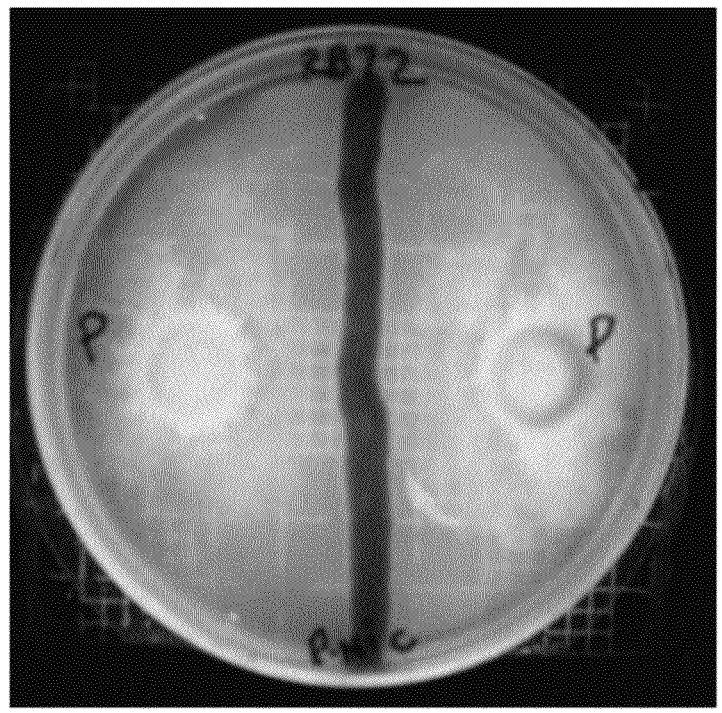
FIG. 6 is a photograph of a representative Petri dish illustrating in vitro growth inhibition of *Phytophthora nicotianae* by *Streptomyces scopuliridis* strain RB72.

As set forth in Table 2, growth inhibition of *P. nicotianae* was rated as 73.44%. FIG. 6 is a photograph of a representative Petri dish showing growth inhibition of *P. nicotianae*.

Example 7

Inhibition of *Clavibacter michiganensis* subsp. *insidiosus*

This example gives an illustration of the inhibitory activity of *Streptomyces scopuliridis* strain RB72, according to the present invention, on the bacterial plant pathogen, *Clavibacter michiganensis* subsp. *insidiosus*.

Figure 7:
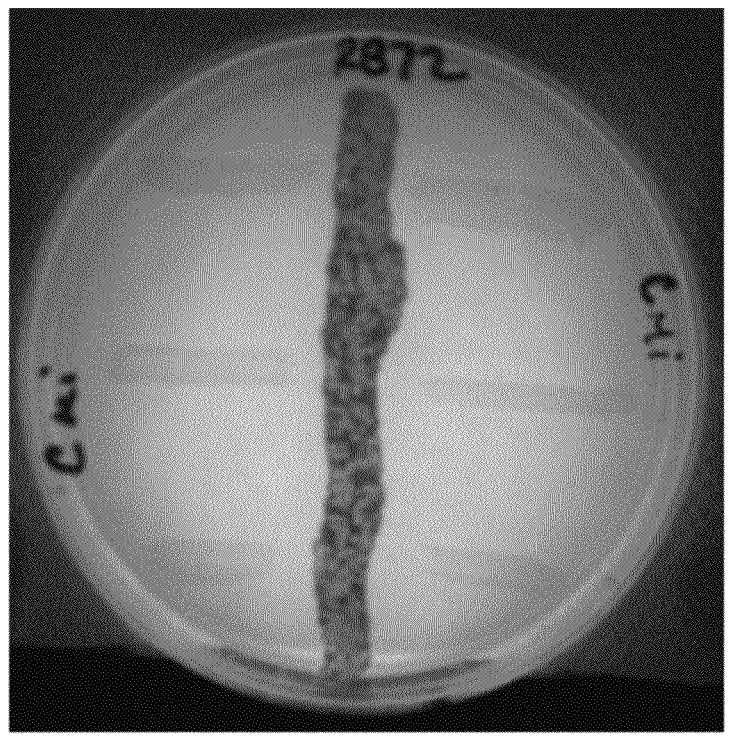
FIG. 7 is a photograph of a representative Petri dish illustrating in vitro growth inhibition of *Clavibacter michiganensis* subsp. *insidiosus* by *Streptomyces scopuliridis* strain RB72.

As set forth in Table 2, growth inhibition of *C. michiganensis* subsp. *insidiosus* was rated as "strong." FIG. 7 is a photograph of a representative Petri dish showing growth inhibition of *C. michiganensis* subsp. *insidiosus*.

Example 8

Inhibition of *Clavibacter michiganensis* subsp. *michiganensis*

This example gives an illustration of the inhibitory activity of *Streptomyces scopuliridis* strain RB72, according to the present invention, on the bacterial plant pathogen, *Clavibacter michiganensis* subsp. *michiganensis*.

Figure 8:
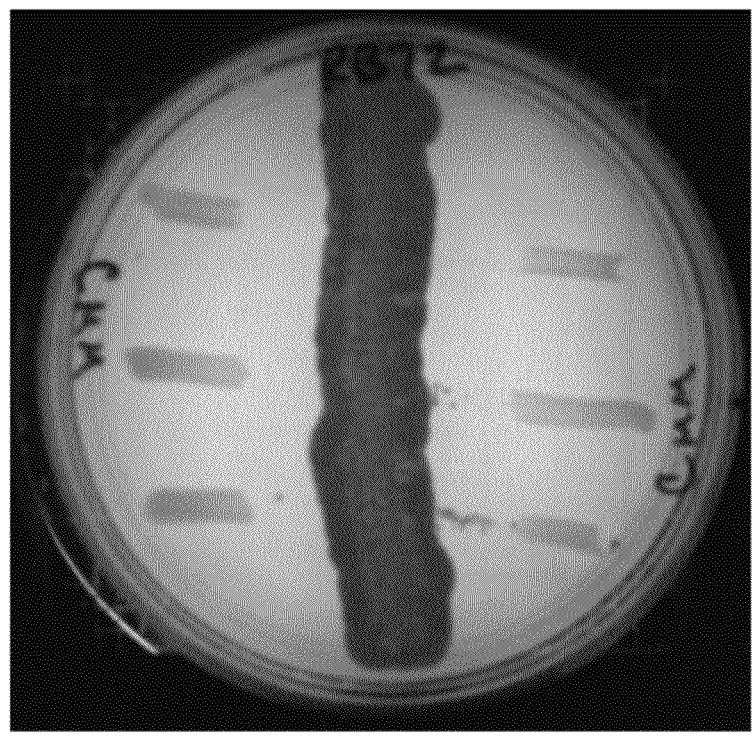
FIG. 8 is a photograph of a representative Petri dish illustrating in vitro growth inhibition of *Clavibacter michiganensis* subsp. *michiganensis* by *Streptomyces scopuliridis* strain RB72.

As set forth in Table 2, growth inhibition of *C. michiganensis* subsp. *insidiosus* was rated as "very strong." FIG. 8 is a photograph of a representative Petri dish showing growth inhibition of *C. michiganensis* subsp. *michiganensis*.

Example 9

Bacteriolytic Activity Against *Xanthomonas campestris*

This example gives an illustration of the bacteriolytic effect of *Streptomcyes scopuliridis* strain RB72, according to the present invention, on the bacterial plant pathogen *Xanthomonas campestris*.

As set forth in Table 3, lysis of heat-killed *Xanthomonas campestris* was rated as "complete inhibition," indicating that all of the cells in the agar were lysed resulting in a full clearing of the plate.

TABLE 3

Bacterial Heat-killed Cell Lysis by *Streptomyces scopuliridis* Strain RB72.

| Phytopathogen | Cell Lysis Results |
| --- | --- |
| *Xanthomonas campestris* | Complete inhibition |
| *Pseudomonas syringae* | Moderate inhibition |
| *Erwinia amylovora* | Complete inhibition |
| *Clavibacter michiganensis* subsp. *michiganensis* | Complete inhibition |
| *Clavibacter michiganensis* subsp. *insidiosis* | Complete inhibition |

Bacterial cell lysis was monitored over time. Once active growth of *Streptomyces scopuliridis* strain RB72 was noted, the zone of lysis became visible. Results reported as complete inhibition indicate that all of the cells in the agar were lysed, resulting in a full clearing of the plate. Results reported as moderate inhibition indicate that a definite zone of lysis was observed but that full lysis of the entire plate did not occur over a three week period. All bacterial strains tested were sensitive to the bacteriolytic enzyme produced by *Streptomyces scopuliridis* strain RB72.

Example 10

Bacteriolytic Activity Against *Pseudomonas syringae*

This example gives an illustration of the bacteriolytic effect of *Streptomcyes scopuliridis* strain RB72, according to the present invention, on the bacterial plant pathogen *Pseudomonas syringae*.

As set forth in Table 3, lysis of heat-killed *Pseudomonas syringae* was rated as "moderate inhibition," indicating that not all of the cells in the agar were lysed resulting in a definite zone of lysis.

Example 11

Bacteriolytic Activity Against *Erwinia amylovora*

This example gives an illustration of the bacteriolytic effect of *Streptomcyes scopuliridis* strain RB72, according to the present invention, on the bacterial plant pathogen *Erwinia amylovora*.

As set forth in Table 3, lysis of heat-killed *Erwinia amylovora* was rated as "complete inhibition," indicating that all of the cells in the agar were lysed resulting in a full clearing of the plate.

Example 12

Bacteriolytic Activity Against *Clavibacter michiganensis* subsp. *michiganensis*

This example gives an illustration of the bacteriolytic effect of *Streptomyces scopuliridis* strain RB72, according to the present invention, on the bacterial plant pathogen *Clavibacter michiganensis* subsp. *michiganensis*.

As set forth in Table 3, lysis of heat-killed *Clavibacter michiganensis* subsp. *michiganensis* was rated as "complete inhibition," indicating that all of the cells in the agar were lysed resulting in a full clearing of the plate.

Example 13

Bacteriolytic Activity Against *Clavibacter michiganensis* subsp. insidiosus

This example gives an illustration of the bacteriolytic effect of *Streptomyces scopuliridis* strain RB72, according to the present invention, on the bacterial plant pathogen *Clavibacter michiganensis* subsp. *insidiosus*.

As set forth in Table 3, lysis of heat-killed *Clavibacter michiganensis* subsp. *insidiosus* was rated as "complete inhibition," indicating that all of the cells in the agar were lysed resulting in a full clearing of the plate.

II. In Vivo Suppression of Foliar Bacterial Diseases
Materials and Methods for Examples 14-15
Suppression of Foliar Bacterial Diseases: Preparation of Bacterial Inocula Live bacterial cell inoculum was produced in one of three different broth culture media for each of the bacterial strains used in foliar bacterial disease suppression bioassays. These broth media were Luria-Bertani broth (LBB), nutrient brewers yeast broth (NBYB), SYZ broth (SYZB). LBB was prepared by dissolving 25 g L-B Broth (Fisher Scientific) in 1 L de-ionized water and autoclaving (121° C. at 3 bar) this solution for 30 min. in closed borosilicate flasks. NBYB was prepared by dissolving the following ingredients in de-ionized water brought to 1-L total volume and autoclaved as described above: 8 g Nutrient Broth (Fisher Scientific), 2 g Yeast Extract (Fisher Scientific), 5 g Dextrose (Fisher Scientific), 0.5 g Monobasic Potassium Phosphate (Fisher Scientific), 0.25 g Magnesium sulfate heptahydrate (Fisher Scientific). SYZB was prepared by dissolving the following ingredients in de-ionized water brought to 1-L total volume and autoclaved as described above: Soluble starch 15 g (Fisher Scientific), 2 g Yeast extract (Fisher Scientific), 4 g NZ-Amine (Amresco), 2 g Dextrose (Fisher Scientific).

The phytopathogenic bacterial strains, *Pseudomonas tomato* pv. *tomato* strain 10-001 and *Clavibacter michiganensis* subsp. *michiganensis* strain 02-001, were obtained from Cornell University, Department of Plant Pathology and Plant-Microbe Biology, Ithaca N.Y. Cryogenic cultures of all bacterial strains used in the foliar bacterial disease bioassays were prepared by aseptically suspending live cells of each bacterial strain in sterile cryovials containing 20% glycerol. These cryovials were immediately frozen at −80° C. until needed for inoculation of broth culture media and were then immediately returned to −80° C. until needed again. Inocula of bacterial strains were produced by aseptically inoculating the appropriate autoclaved broth with cells from their specific cryoculture vials. All samples were handled using standard aseptic techniques to maintain purity and prevent cross contamination.

RB72 and pathogens were cultured in flasks of the appropriate broth for 36-72 hours at 24° C.-27° C. on a shaker table (90 RPM). RB72 and each bacterial pathogen were then centrifuged at 5×G for 5 minutes after which the supernatant was gently removed and discarded appropriately. The resulting pellet of RB72 cells was resuspended in 50 mL autoclaved tap water. This concentrated RB72 inoculum supspension was gradually added to 1 L autoclaved tap water until a concentration of $1\times10^8$ CFU RB72 $mL^{-1}$ was reached.

Suppression of Foliar Bacterial Diseases: Growing Media

A potting medium was used that was composed of a 70:15:15 ratio (v/v) of dark peat, coarse horticultural grade perlite, and D3 fine vermiculite. The mix was amended further with 5.4 g Dolomitic lime, 3.5 g $CaCO_3$, 1.1 g $KNO_3$, 1.1 g Gypsum, and 1.1 g superphosphate (0-45-0) (each expressed per liter). Slow release fertilizer (Osmocote 15-9-12, N—P—K plus minors, The Scotts Company) was incorporated before planting into the potting media at a rate of 12.5 g per liter.

Suppression of Foliar Bacterial Diseases: Application and Evaluation

The tomato (*Solanum lycopersicum* L.) cultivars 'Yellow Pear' and 'Oregon Spring' were used in these studies. Seeds were germinated in a seedling tray and were transplanted into 10-cm-diameter polystyrene pots 4 weeks after planting. The plants were grown in a greenhouse between 18° C.-32° C. and received 14-16 hours of sunlight per day. They were watered as needed via overhead irrigation.

Immediately prior to application on plants, 20 µL/L Silwet ECO (Momentive) was mixed into each RB72 inoculum suspension to provide proper coverage and spreading on target leaf surfaces. Fresh RB72 inoculum was applied to the upper and lower leaf surfaces until runoff of foliage of plants designated for RB72 treatment 5 weeks after seeding. Natural control plants (i.e., those designated not to receive RB72) only received autoclaved tap water containing Silwet ECO (20 µL/L). After 24 hours, all plants were placed in a mist tent for 4 hours. At this time, plant were removed from the mist tent and the foliage of each was completely sprayed until run-off with autoclaved tap water or $3.3\times10^4$, $3.3\times10^5$ or $3.3\times10^6$ CFU/mL of either *Clavibacter michiganensis* subsp. *michiganensis* or *Pseudomonas tomato* pv. tomato. For the *Pseudomonas* test, only the variety "Oregon Spring' was tested. Sprayed plants were immediately returned to the mist tent where they remained in high relative humidity (<90%) for 12 hours to promote infection and disease development. After this period, plants were returned to their original locations outside of the mist tent until rating.

Percent leaf area affected (LAA) by lesions was rated 13 days after pathogen application. After examination, the two true leaves on each plant that exhibited the most severe disease symptoms were rated according to a 1-6 rating scale in which: 1=symptomless leaf, 2=few lesions to 10% LAA, 3=10%-25% LAA, 4=25%-50% LAA, 5=50%-75% LAA, and 6=75%-100% LAA or dead leaf.

Suppression of Foliar Bacterial Diseases: Experimental Design and Statistical Analysis All bioassays were performed according to a completely randomized design. Each treatment was replicated 5 times (five pots per treatment). Treatment effects were evaluated using one-way analysis of variance (ANOVA). Minitab statistical software (Release 14, Minitab, Inc., State College, Pa.) was used for all analyses. If a significant F-test was obtained among treatments, significance of difference among means was determined using Fisher's least significant difference test.

Example 14

Efficacy of RB72 Against Bacterial Canker, *Clavibacter michiganensis* subsp. *michiganensis*, on Two Cultivars of Tomato This example illustrates the efficacy of *Streptomyces scopuliridis* strain RB72, according to the present invention, to reduce disease caused by the bacterial plant pathogen *C. michiganensis* subsp. *michiganensis* on tomato.

As set forth in Table 4, *Streptomyces scopuliridis* strain RB72 reduced disease caused by the highest application rate of *C. michiganensis* subsp. *michiganensis* by 85% on tomato, *Solanum lycopersicum* L. var. 'Oregon Spring.' Table 4 shows the effect of *Streptomyces scopuliridis* strain RB72 foliar pretreatment on the severity of Bacterial Canker of Tomato caused by *Clavibacter michiganensis* subsp. *michiganensis* on *Solanum lycopersicum* L. var. 'Oregon Spring.'

TABLE 4

| C. michiganensis subsp. michiganensis inoculum | Percent Leaf Area Affected by Lesions | |
|---|---|---|
| | Water (Control) | S. scopuliridis strain RB72 |
| None | 1.5 | 0.0 |
| $3.3 \times 10^4$ CFU ml$^{-1}$ | 4.5 | 0.0 |
| $3.3 \times 10^5$ CFU ml$^{-1}$ | 10.0 | 4.5 |
| $3.3 \times 10^6$ CFU ml$^{-1}$ | 33.5 | 5.0 |
| LSD$_{0.05}$ | | 3.5 |

As set forth in Table 5, *Streptomyces scopuliridis* strain RB72 reduced disease caused by the highest inoculum density of *C. michiganensis* supsp. *michiganensis* by 84% on tomato, *Solanum lycopersicum* L. var. 'Yellow Pear.' Table 5 shows the effect of *Streptomyces scopuliridis* strain RB72 foliar pretreatment on the severity of Bacterial Canker of Tomato caused by *Clavibacter michiganensis* subsp. *michiganensis* on *Solanum lycopersicum* L. var. 'Yellow Pear.'

TABLE 5

| C. michiganensis subsp. michiganensis inoculum | Percent Leaf Area Affected by Lesions | |
|---|---|---|
| | Water (Control) | S. scopuliridis strain RB72 |
| None | 0.0 | 0.0 |
| $3.3 \times 10^4$ CFU ml$^{-1}$ | 0.0 | 0.0 |
| $3.3 \times 10^5$ CFU ml$^{-1}$ | 2.0 | 1.0 |

TABLE 5-continued

| C. michiganensis subsp. michiganensis inoculum | Percent Leaf Area Affected by Lesions | |
|---|---|---|
| | Water (Control) | S. scopuliridis strain RB72 |
| $3.3 \times 10^6$ CFU ml$^{-1}$ | 27.5 | 4.5 |
| LSD$_{0.05}$ | | 3.5 |

Example 15

Efficacy of RB72 Against Bacterial Speck, *Pseudomonas tomato* pv. tomato on One Cultivar of Tomato This example illustrates the efficacy of *Streptomyces scopuliridis* strain RB72, according to the present invention, to reduce disease caused by the bacterial plant pathogen *Pseudomonas tomato* pv. tomato on tomato.

As set forth in Table 6, *Streptomyces scopuliridis* strain RB72 reduced disease caused by the highest inoculum density of *P. tomato* by 50% on tomato, *Solanum lycopersicum* L. var. 'Oregon Spring.' Table 6 shows the effect of *Streptomyces scopuliridis* strain RB72 foliar pretreatment on the severity of Bacterial Speck of Tomato caused by *P. tomato* on *Solanum lycopersicum* L. var. 'Oregon Spring.'

TABLE 6

| Pseudomonas tomato pv. tomato inoculum | Percent Leaf Area Affected by Lesions | |
|---|---|---|
| | Water (Control) | S. scopuliridis strain RB72 |
| None | 0.0 | 0.0 |
| $3.3 \times 10^4$ CFU ml$^{-1}$ | 7.5 | 5.0 |
| $3.3 \times 10^5$ CFU ml$^{-1}$ | 12.5 | 8.8 |
| $3.3 \times 10^6$ CFU ml$^{-1}$ | 15.0 | 7.5 |
| LSD$_{0.05}$ | | 4.0 |

III. In Vivo Suppression of Soil Fungal Diseases
Materials and Methods for Examples 16-18
Suppression of Soil Fungal Diseases: Preparation of RB72 Inoculum A combination of RB72 and vermiculite was used to treat potting media in these tests and prepared in the following manner. SYZ broth medium was mixed and autoclaved for 30 minutes at 121° C. The SYZ broth was cooled overnight to room temperature. An RB72 colony was streaked across a YDC media Petri plate and incubated for 4-5 days at ~30° C. The RB72 colony streak was aseptically scraped from the Petri plate and added to 20 mL of sterile DI water in a 50 mL centrifuge tube. This mixture was added to the SYZ broth and allowed to incubate on an orbital shaker (90 rpm) at 25° C. for 2 weeks. The entire 250 mL of RB72 inoculum in SYZ broth was added to 1 kg of autoclaved vermiculite and mixed thoroughly by shaking vigorously. Three grams of this preparation was removed and enumerated by dilution plating on Petri plates containing SYZ agar (SYZA) medium (SYZ broth containing 15 g agar).

Suppression of Soil Fungal Diseases: Preparation of Fusarium, Phytophthora, and Rhizoctonia Inocula Phytopathogenic fungal strains were obtained and maintained as described above. One colonized Petri plate containing *F. oxysporum* f. sp. *lycopersici* or *Phytophthora nicotianae* or *Rhizoctonia solani* was aseptically scraped from the Petri plate and blended into 1 L of autoclaved DI water. Two-hundred and fifty mL of the pathogen slurry was added to 1 Kg of autoclaved vermiculite, mixed thoroughly, and refrigerated until use. This mixture was into the potting media at a rate of 5% (w/w).

Suppression of Soil Fungal Diseases: Application and Evaluation

Sunshine MVP (Sun Gro Horticulture), a standard Sphagnum peat-based potting medium, was be used for all bioassays. To minimize or eliminate populations of naturally occurring disease-suppressive microflora that sometimes colonize potting media after formulation, all potting mixes used in bioassays were hydrated to 50% water-holding capacity and heat-treated at 60° C. for 5 days immediately prior to each bioassay.

Seedling bioassays were used to assess effects of RB72 against seedling damping-off caused by *R. solani*, and *P. nicotianae*, and wilt caused by *F. oxysporum*. Plants used in these assays were tomato (*Solanum lycopersicum* 'Beefsteak') and pepper (*Capsicum annuum* 'Big Red'). For each assay, 10 seeds were planted into each of 5, 25.4 cm pots containing the appropriate treated mix. The untreated check pots contained growing medium with blank, autoclaved vermiculite incorporated at 10% (w/w); the inoculated check had pathogen-infested vermiculite incorporated at a rate of 5% (w/w) and sterile vermiculite at 10% (w/w); the RB72+pathogen inoculum treatment contained both the RB72-infested vermiculite at 10% (w/w) and pathogen-inoculated vermiculite at 5% (w/w).

Approximately 30 days after planting, the bioassay was terminated; the dry root and shoot biomass of each plant from all treatments were recorded by severing the root from the shoot at the soil line, washing off the remaining dirt and debris, and allowing them to dry overnight at 60° C. Cumulative weights for each pot were recorded.

Suppression of Soil Fungal Diseases: Experimental Design and Statistical Analysis The dry foliar biomass and dry root biomass were measured and analyzed for each pot containing 10 tomato seedlings per potting mix treatment (n=3). Mean dry foliar biomass and dry root biomass values were determined and treatment effects were evaluated by one-way ANOVA using Minitab Statistical Software (version 15; Minitab Inc.). If a significant F test was obtained among treatments, significance of difference among means was determined using Fisher's least significant difference test.

Example 16

Efficacy of RB72 Against *Fusarium* Damping Off, *Fusarium oxysporum* f. sp. *lycopersici* on Tomato This example gives an illustration of the efficacy of *Streptomyces scopuliridis* strain RB72, according to the present invention, to reduce disease symptoms caused by the fungal pathogen, *Fusarium oxysporum* f. sp. *lycopersici*, on tomato.

As set forth in Table 7, the potting mix containing *S. scopuliridis* strain RB72 suppressed negative effects on foliar biomass and root biomass caused by infestation with *Fusarium oxysporum* f. sp. *lycopersici*. Table 7 shows the effect of *S. scopuliridis* strain RB72 potting mix treatment on the impact of damping-off caused by *Fusarium oxysporum* f. sp. *lycopersici* on mean dry foliar and dry root biomass per pot of tomato seedlings (*Solanum lycopersicum* L. var. 'Beefsteak').

TABLE 7

| Potting Mix Treatment | Mean Dry Foliar Biomass (g/pot) | Mean Dry Root Biomass (g/pot) |
| --- | --- | --- |
| Natural Control | 3.8 | 0.26 |
| Natural + *F. oxysporum* f.sp. *lycopersici* | 1.5 | 0.11 |
| RB72 + *F. oxysporum* f.sp. *lycopersici* | 3.8 | 0.26 |
| LSD$_{0.05}$ | 0.8 | 0.10 |

Example 17

Efficacy of RB72 Against Phytophthora Root Rot, *Phytophthora nicotianae* on Pepper This example gives an illustration of the efficacy of *Streptomyces scopuliridis* strain RB72, according to the present invention, to reduce disease symptoms caused by the fungal pathogen, *Phytophthora nicotianae*, on pepper.

As set forth in Table 8, the potting containing *S. scopuliridis* strain RB72 suppresses negative effects on foliar biomass and root biomass caused by infestation with *Phytophthora nicotianae*. Table 8 shows the effect of *S. scopuliridis* strain RB72 potting mix treatment on the impact of damping-off caused by *Fusarium oxysporum* f. sp. *lycopersici* on mean dry foliar and dry root biomass per pot of pepper seedlings (*Capsicum annuum* var. 'Big Red').

TABLE 8

| Potting Mix Treatment | Mean Dry Foliar Biomass (g/pot) | Mean Dry Root Biomass (g/pot) |
| --- | --- | --- |
| Natural Control | 7.5 | 1.4 |
| Natural + *P. nicotianae* | 6.0 | 0.9 |
| RB72 + *P. nicotianae* | 8.0 | 1.7 |
| LSD$_{0.05}$ | 1.0 | 0.3 |

Example 18

Efficacy of RB72 Against Rhizoctonia Damping Off, *Rhizoctonia solani*, on Pepper This example gives an illustration of the efficacy of *Streptomyces scopuliridis* strain RB72, according to the present invention, to reduce disease symptoms caused by the fungal pathogen, *Rhizoctonia solani* on pepper.

As set forth in Table 9, the potting mix with *S. scopuliridis* strain RB72 suppresses negative effects on foliar biomass and root biomass caused by infestation with *Rhizoctonia solani*, as measured by dry foliar biomass and dry root biomass. Table 9 shows the effect of *S. scopuliridis* strain RB72 potting mix treatment on the impact of damping-off caused by *Rhizoctonia solani* on mean dry foliar and dry root biomass per pot of pepper seedlings (*Capsicum annuum* var. 'Big Red').

TABLE 9

| Potting Mix Treatment | Mean Dry Foliar Biomass (g/pot) | Mean Dry Root Biomass (g/pot) |
| --- | --- | --- |
| Natural Control | 7.6 | 1.4 |
| Natural + *R. solani* | 5.7 | 0.8 |
| RB72 + *R. solani* | 7.8 | 1.7 |
| LSD$_{0.05}$ | 1.6 | 0.4 |

IV. Plant Growth Enhancement Effect of *Streptomyces scopuliridis* strain RB72

Materials and Methods for Example 19

Growth Enhancement Effect: Streptomyces scopuliridis Strain RB72 Granular Inoculum Preparation and Incorporation into Potting Medium Granular inoculum of *S. scopuliridis* strain RB72 was prepared for all plant-growth promotion experiments according to the following protocol. An RB72 colony was streaked across an YDC media Petri plate and incubated for 4-5 days at 27-30° C. SYZB (250 ml) was prepared and autoclaved in closed borosilicate flasks as described above. After autoclaved SYZB medium was allowed to cool, an RB72 colony streak was scraped from the Petri plate using aseptic technique and was suspended in 20 mL of autoclaved de-ionized water in a sterile 50 mL centrifuge tube. This suspension was added to the SYZB media and incubated at 24-27 C on a shaker table (90 rpm) for 2 weeks Immediately thereafter, 250 mL of an $8.8 \times 10^6$ CFU/mL suspension of cells from the RB72 broth culture was thoroughly mixed with 1 kg autoclaved (121° C. at 3 bar for 45 min.) fine vermiculite by shaking in a sterile polyethylene bag. The resulting granular inoculum formulation was incorporated into a typical Sphagnum peat-based potting mix used by professional horticultural growers (MetroMix 360, SunGro Horticulture) using a cement mixer at a rate of 100 g RB72 vermiculite inoculum per 900 g potting medium. This method yields a potting mix (referred hereafter as RB72 mix) with $2.2 \times 10^5$ CFU RB72/g fresh weight potting mix.

A control potting mix lacking RB72 inoculum (referred hereafter as natural mix) was also prepared for each plant growth promotion bioassay by mixing 250 mL autoclaved de-ionized water with 1 kg autoclaved vermiculite and blending this vermiculite preparation with the potting mix described above at a rate of 100 g vermiculite preparation per 900 g potting mix.

Growth Enhancement Effect: Experimental Design, Bioassay, and Statistical Analysis Ten bell pepper (*Capsicum annuum* L. var. 'Big Red') seeds were sown into three, 10" pots containing either natural mix or RB72 mix. All pots were watered at seeding an as needed thereafter with a 100 ppm Nitrogen nutrient solution derived from a 20-20-20 water-soluble fertilizer (Jack's Classic). Pots were then be placed into a 25-27° C. growth chamber illuminated 12 hours daily by fluorescent lighting. After 7 weeks, all plants were carefully cut at the soil surface and retained for measuring foliar dry weight per pot. Foliar dry weight measurements represent directly report the extent of plant growth by indicating the actual amount of foliar biomass generated by plants grown in the different potting mix treatments. Plants removed from each pot were pooled together, dried in a 60 C drying oven for 48 h, and weighed to determine foliar dry weight per pot per potting mix treatment.

Foliar dry weights recorded for each pot for each potting mix treatment were analyzed by one-way ANOVA using Minitab Statistical Software (version 14; Minitab Inc.). Standard error of the mean foliar dry weight values per pot per treatment were calculated to determine differences among potting mix treatments.

Example 19

Growth Enhancement of RB72 on Pepper Seedlings

Figure 9:
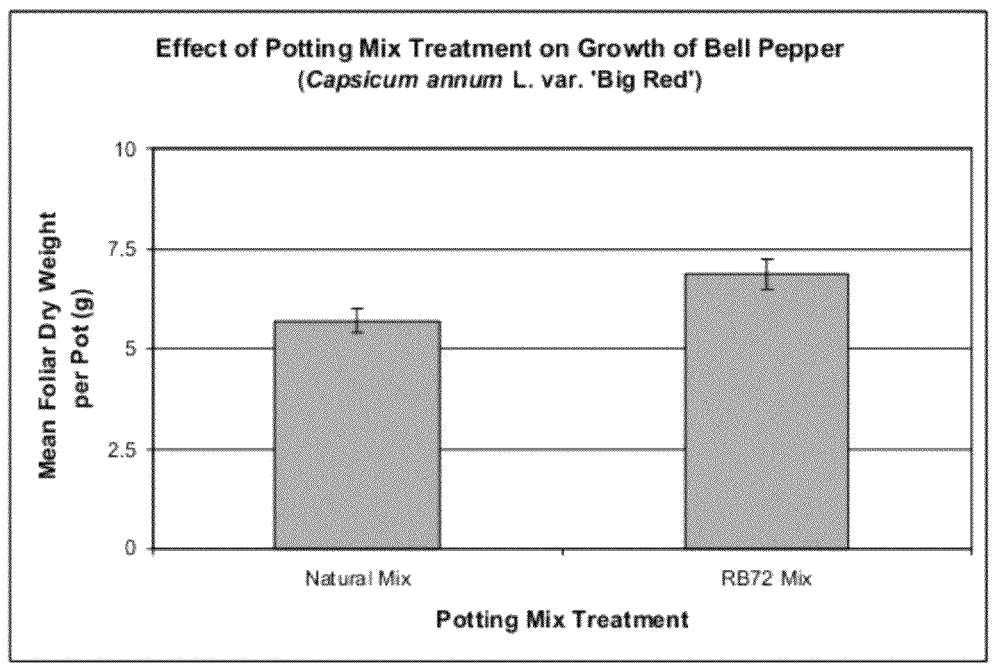
FIG. 9 is a bar graph of experimental results showing the effect of potting mix treatment with *Streptomyces scopuliridis* strain RB72 on growth of bell pepper seedlings as determined by mean foliar dry weight per pot. Bars indicate the standard error of the mean for each treatment.

This example gives an illustration of the properties of *Streptomyces scopuliridis* strain RB72, according to the present invention, to increase plant growth. As shown in FIG. 9, bell pepper plants seeded and grown in RB72 mix produced significantly greater biomass (almost 21% more) than those produced in natural mix.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

---

What is claimed:

1. A planting composition comprising:
a growing media selected from the group consisting of artificial soilless growing media containing organic and/or inorganic ingredients, hydroponic nutrient growth solutions, and mixtures thereof; and a microorganism, *Streptomyces scopuliridis* strain RB72, accession number DSM 41917, or a polypeptide consisting of the amino acid sequence of SEQ ID NO: 1.

2. The planting composition of claim 1, wherein the planting composition comprises the *Streptomyces scopuliridis* strain RB72.

3. The planting composition of claim 1, wherein the planting composition comprises the polypeptide.

4. The planting composition of claim 1, wherein the planting composition further comprises a carrier.

5. The planting composition of claim 4, wherein the carrier is selected from the group consisting of water, aqueous solutions, slurries, and powders.

6. The planting composition of claim 1, wherein the planting composition further comprises additives selected from the group consisting of fertilizer, insecticide, fungicide, nematicide, organic fertilizer, bioinsecticide, biofungicide, bionematicide, stickers, spreaders, surfactants, dispersants, humectants, U.V. protectants, and mixtures thereof.

* * * * *